US010456488B2

United States Patent
Bilenko et al.

(10) Patent No.: US 10,456,488 B2
(45) Date of Patent: Oct. 29, 2019

(54) ULTRAVIOLET TRANSPARENT STRUCTURE FOR ULTRAVIOLET ILLUMINATION USING SCATTERED AND FOCUSED RADIATION

(71) Applicant: Sensor Electronic Technology, Inc., Columbia, SC (US)

(72) Inventors: Yuri Bilenko, Columbia, SC (US); Alexander Dobrinsky, Silver Springs, MD (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 16/142,927

(22) Filed: Sep. 26, 2018

(65) Prior Publication Data

US 2019/0030196 A1     Jan. 31, 2019

Related U.S. Application Data

(63) Continuation-in-part of application No. 15/911,698, filed on Mar. 5, 2018, which is a continuation of
(Continued)

(51) Int. Cl.
*A61L 2/10*        (2006.01)

(52) U.S. Cl.
CPC .............. *A61L 2/10* (2013.01); *A61L 2202/14* (2013.01)

(58) Field of Classification Search
CPC ..... A61L 2/10; A61L 2/24; A61L 9/20; A61L 2202/14; A23B 7/015; A23L 3/28; A61N 5/0624; B41J 11/002; E05B 1/0069
See application file for complete search history.

(56) References Cited

U.S. PATENT DOCUMENTS

| 6,490,351 B1 | 12/2002 | Roberts |
| 7,553,456 B2 | 6/2009 | Gaska et al. |

(Continued)

OTHER PUBLICATIONS

Purinton, B., U.S. Appl. No. 15/015,539, Notice of Allowance, dated Nov. 1, 2017, 11 pages.
(Continued)

*Primary Examiner* — Brooke Purinton
(74) *Attorney, Agent, or Firm* — LaBatt, LLC

(57) ABSTRACT

A solution for disinfecting an ultraviolet transparent structure and/or an item placed on or near the structure is provided. The solution can utilize a set of ultraviolet radiation sources configured to generate ultraviolet radiation through the internal surface of the ultraviolet transparent structure towards the external surface and out to an ambient environment for disinfection of the external surface and/or a targeted item. A first set of sources can generate a scattered type of radiation that uniformly disinfects the external surface of the ultraviolet transparent structure and a second set of sources can generate a focused type of radiation that disinfects at least one portion of the targeted item. A control system can direct the first set of sources to generate the scattered radiation towards the external surface of the ultraviolet transparent structure and direct the second set of sources to generate the focused radiation at the targeted item.

20 Claims, 17 Drawing Sheets

Related U.S. Application Data application No. 15/015,539, filed on Feb. 4, 2016, now Pat. No. 9,907,869, which is a continuation of application No. 14/640,051, filed on Mar. 6, 2015, now Pat. No. 9,339,571.

(60) Provisional application No. 61/949,650, filed on Mar. 7, 2014.

(56) References Cited

U.S. PATENT DOCUMENTS

| | | | |
|---|---|---|---|
| 8,277,734 | B2 | 10/2012 | Koudymov et al. |
| 8,384,047 | B2 | 2/2013 | Shur et al. |
| 8,431,910 | B1 | 4/2013 | Perry |
| 8,597,569 | B2 | 12/2013 | Gruen et al. |
| 9,042,967 | B2 | 5/2015 | Dacosta et al. |
| 9,142,741 | B2 | 9/2015 | Shatalov et al. |
| 9,339,571 | B2 | 5/2016 | Bilenko et al. |
| 9,459,001 | B2 | 10/2016 | Kjaer et al. |
| 9,907,869 | B2 | 3/2018 | Bilenko et al. |
| 2002/0190220 | A1 | 12/2002 | Sarchese et al. |
| 2005/0072032 | A1 | 4/2005 | McCollum et al. |
| 2005/0184305 | A1 | 8/2005 | Ueda |
| 2005/0218468 | A1 | 10/2005 | Owen et al. |
| 2006/0012285 | A1 | 1/2006 | Matsumoto et al. |
| 2006/0108910 | A1 | 5/2006 | Justel et al. |
| 2006/0195166 | A1 | 8/2006 | Minamoto et al. |
| 2006/0275188 | A1 | 12/2006 | Wei |
| 2009/0032527 | A1 | 2/2009 | Lee et al. |
| 2009/0280035 | A1 | 11/2009 | Koudymov et al. |
| 2010/0296971 | A1 | 11/2010 | Gaska et al. |
| 2011/0291995 | A1 | 12/2011 | Shr et al. |
| 2012/0037536 | A1 | 2/2012 | Lonsdale, II et al. |
| 2013/0004367 | A1 | 1/2013 | Roberts |
| 2013/0045132 | A1 | 2/2013 | Tumanov |
| 2013/0048545 | A1 | 2/2013 | Shatalov et al. |
| 2013/0063922 | A1 | 3/2013 | La Porte et al. |
| 2013/0255100 | A1 | 10/2013 | Valia et al. |
| 2013/0270445 | A1 | 10/2013 | Gaska et al. |
| 2014/0000844 | A1 | 1/2014 | Chandaria |
| 2014/0008675 | A1 | 1/2014 | Shatalov et al. |
| 2014/0016351 | A1 | 1/2014 | Park et al. |
| 2014/0050612 | A1 | 2/2014 | Kneissl et al. |
| 2014/0060094 | A1 | 3/2014 | Shur et al. |
| 2014/0060095 | A1 | 3/2014 | Shur et al. |
| 2014/0060096 | A1 | 3/2014 | Shur et al. |
| 2014/0060104 | A1 | 3/2014 | Shur et al. |
| 2014/0061509 | A1 | 3/2014 | Shur et al. |
| 2014/0183377 | A1 | 7/2014 | Bettles et al. |
| 2014/0202962 | A1 | 7/2014 | Bilenko et al. |
| 2014/0264070 | A1 | 9/2014 | Bettles et al. |
| 2014/0264076 | A1 | 9/2014 | Bettles et al. |
| 2015/0143648 | A1 | 5/2015 | Batey |
| 2016/0151523 | A1 | 6/2016 | Bilenko et al. |
| 2018/0193503 | A1 | 7/2018 | Bilenko et al. |
| 2019/0098842 | A1* | 4/2019 | Barber, III ............ A01G 7/045 |

OTHER PUBLICATIONS

Purinton, B., U.S. Appl. No. 15/015,539, Non-Final Rejection, dated Apr. 21, 2017, 14 pages.

Puriton, B., U.S. Appl. No. 15/015,539, Final Rejection, dated Nov. 16, 2016, 15 pages.

Purinton, B., U.S. Appl. No. 15/015,539, Non-Final Rejection, dated Jul. 5, 2016, 21 pages.

Purinton, B., U.S. Appl. No. 14/640,051, Notice of Allowance, dated Jan. 25, 2016, 6 pages.

Purinton, B., U.S. Appl. No. 14/640,051, Final Office Action 1, dated Nov. 25, 2015, 21 pages.

Purinton, B., U.S. Appl. No. 14/640,051, Office Action 1, dated Aug. 31, 2015, 28 pages.

Lee, Dong Wook, International Application No. PCT/US2015/019086, International Search Report, dated May 29, 2015, 3 pages.

Chinese Application No. 201590000461.7, Notice of Allowance, dated Apr. 28, 2017, 2 pages. (English translation is not available).

Chinese Application No. 201590000461.7, Office Action1, dated Feb. 3, 2017, 2 pages. (English translation is not available.).

Purinton, B., U.S. Appl. No. 15/911,698, Office Action 1, dated May 24, 2019, 16 pages.

* cited by examiner

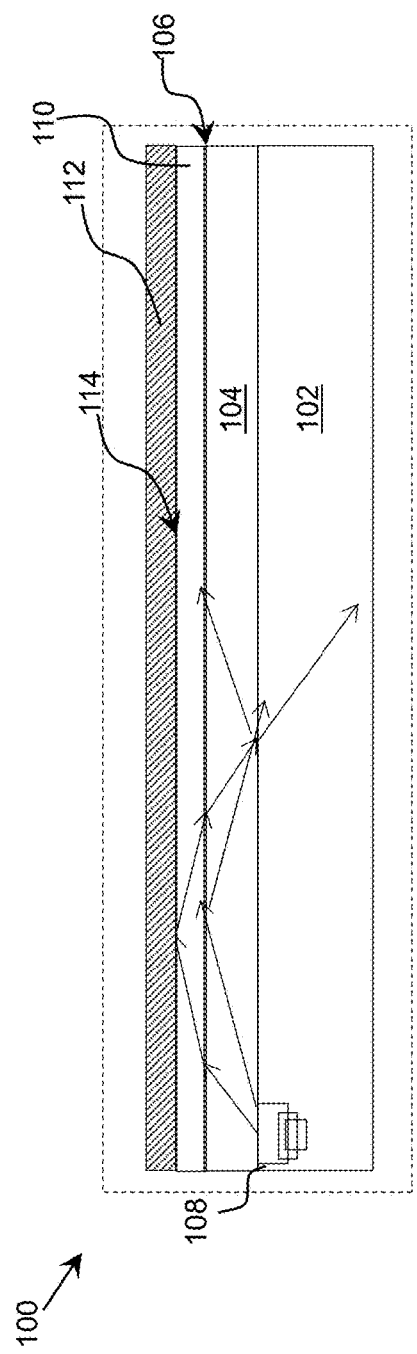
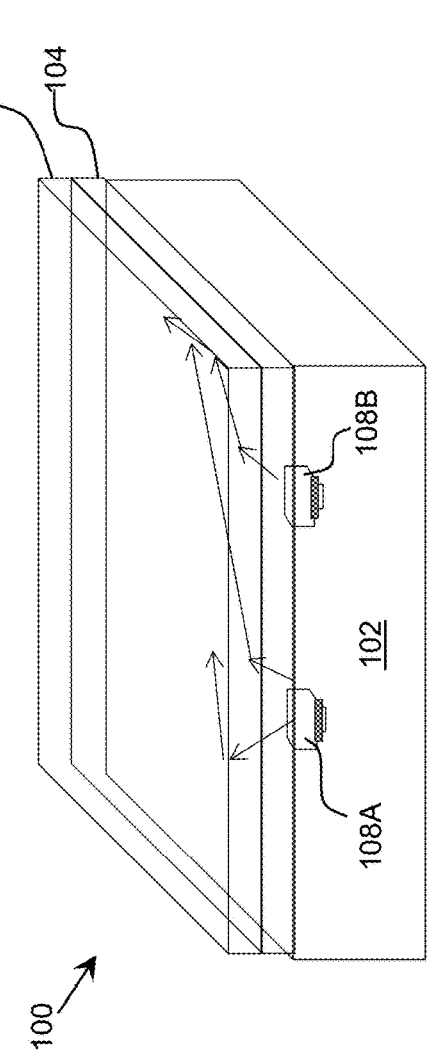

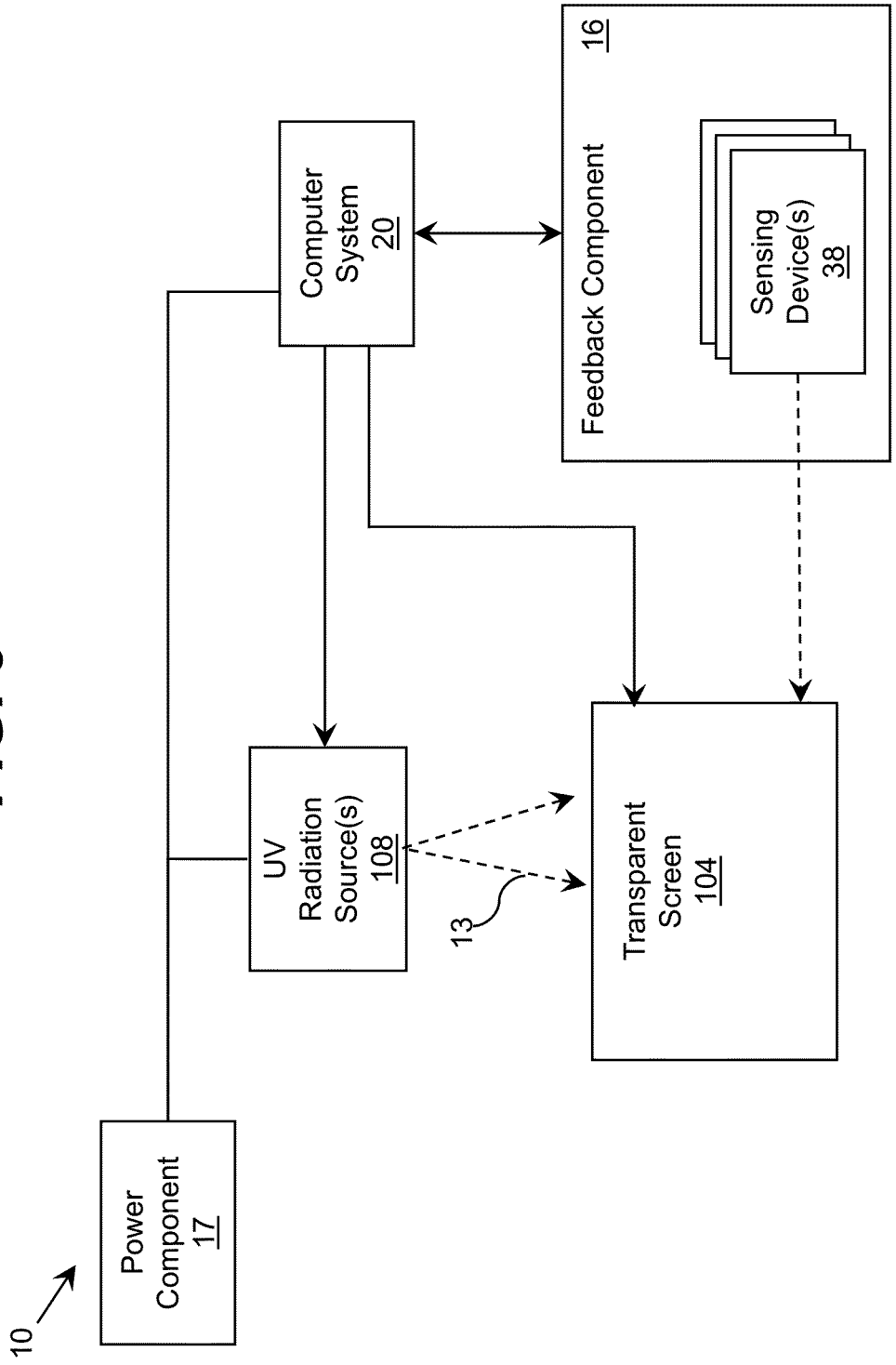

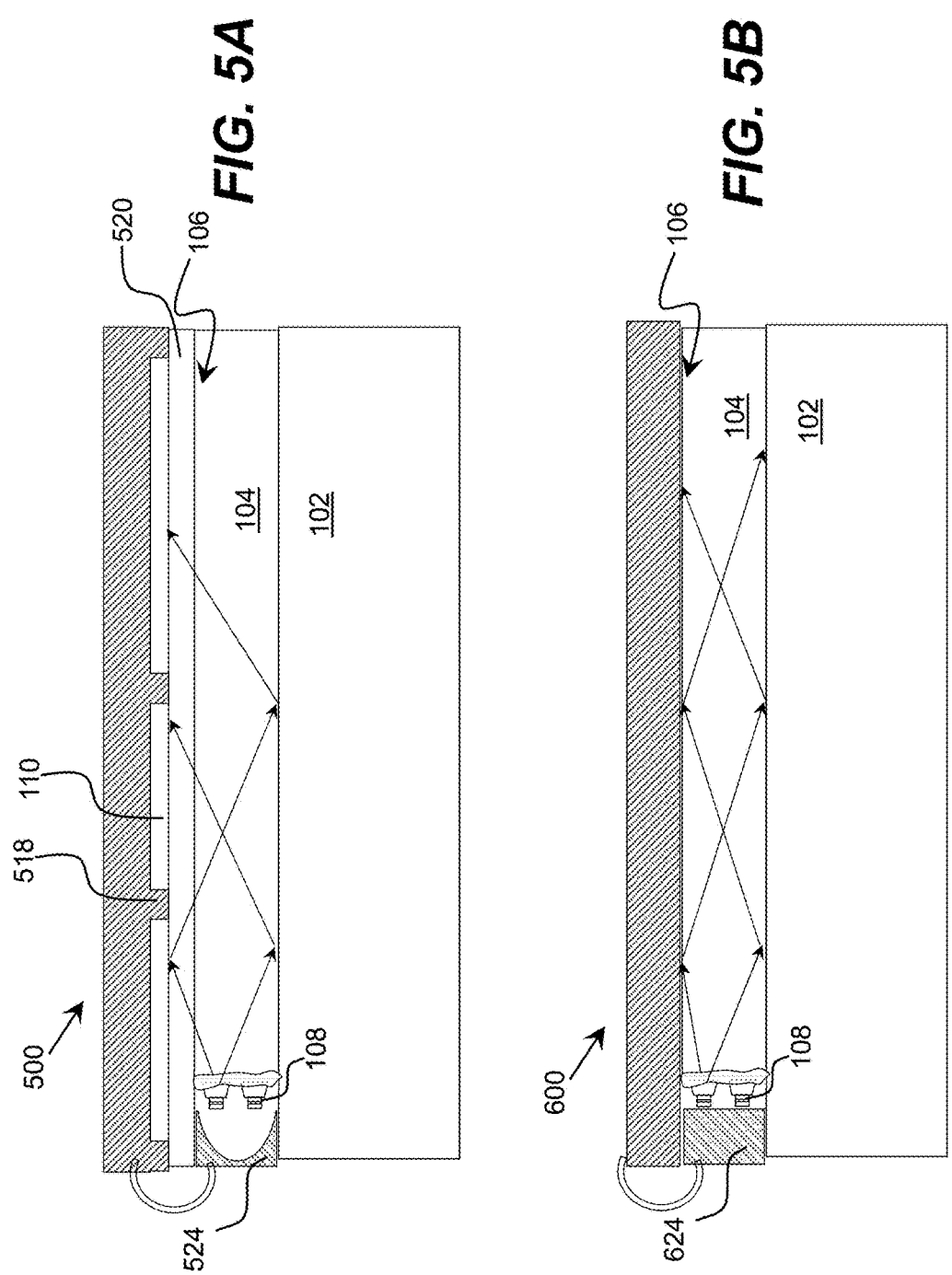

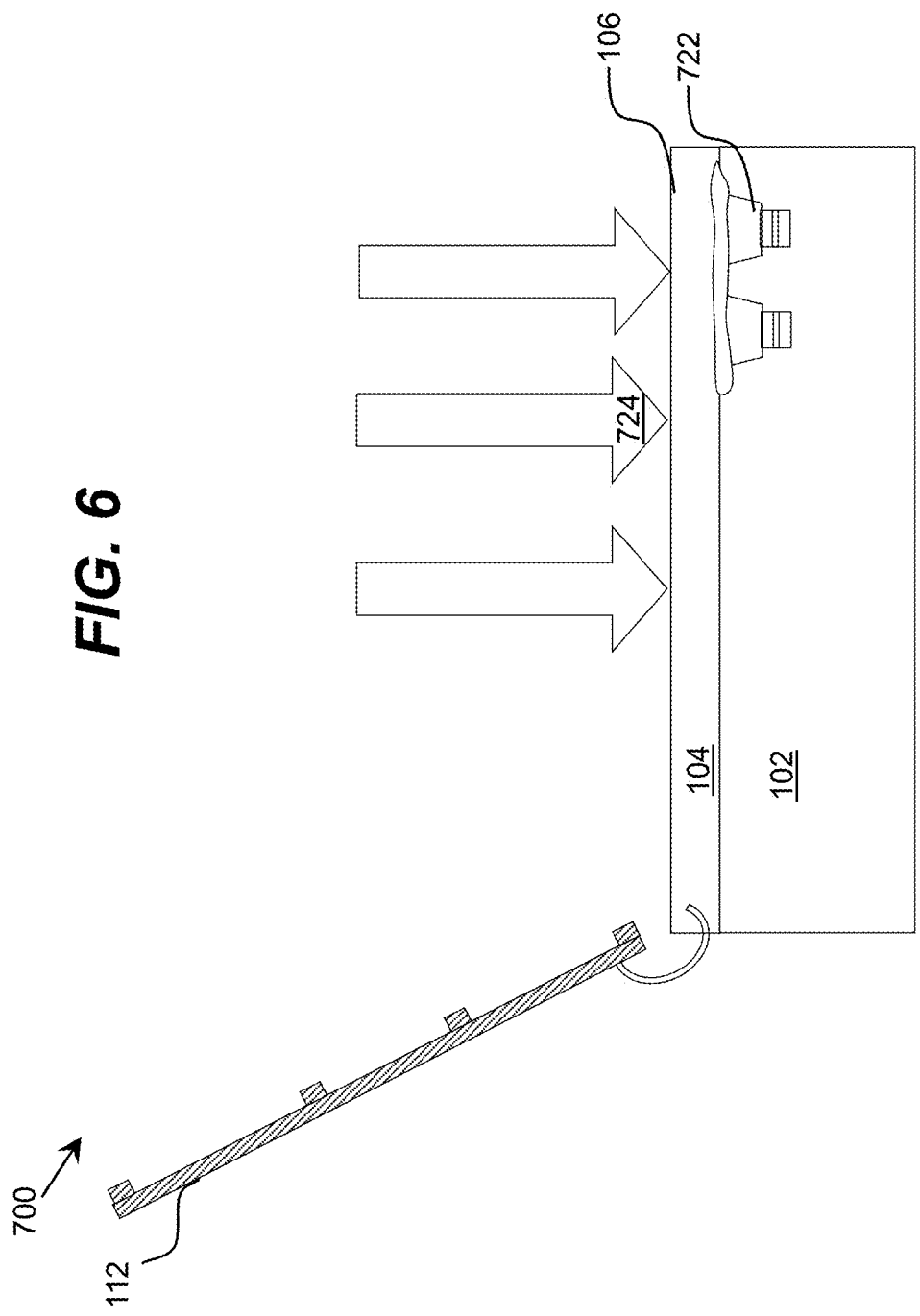

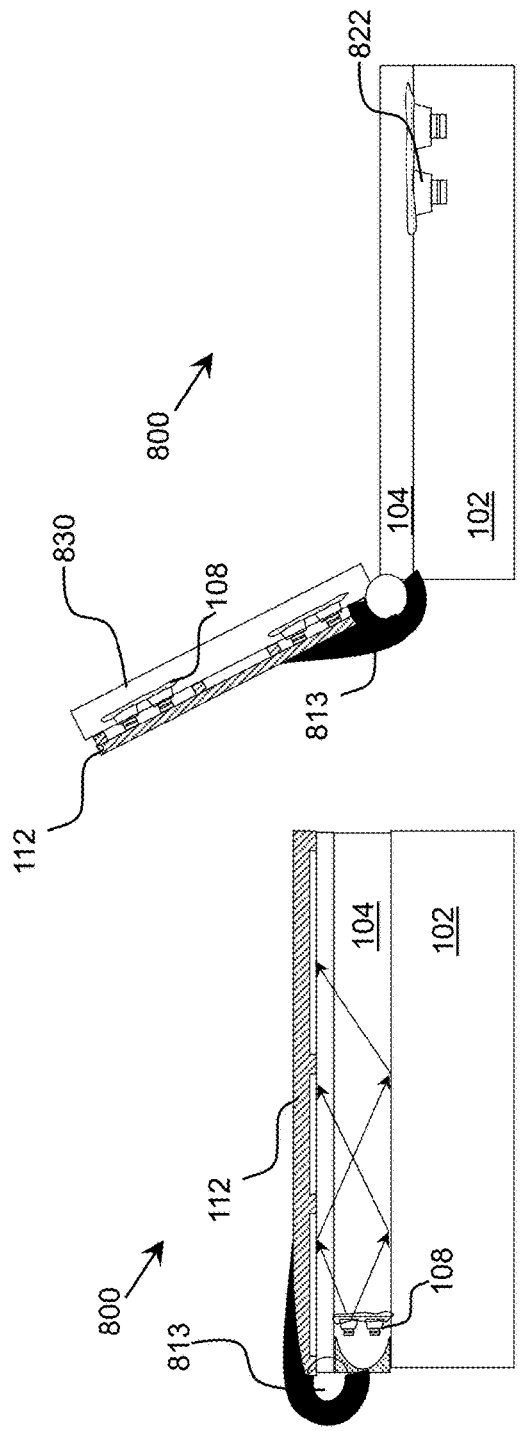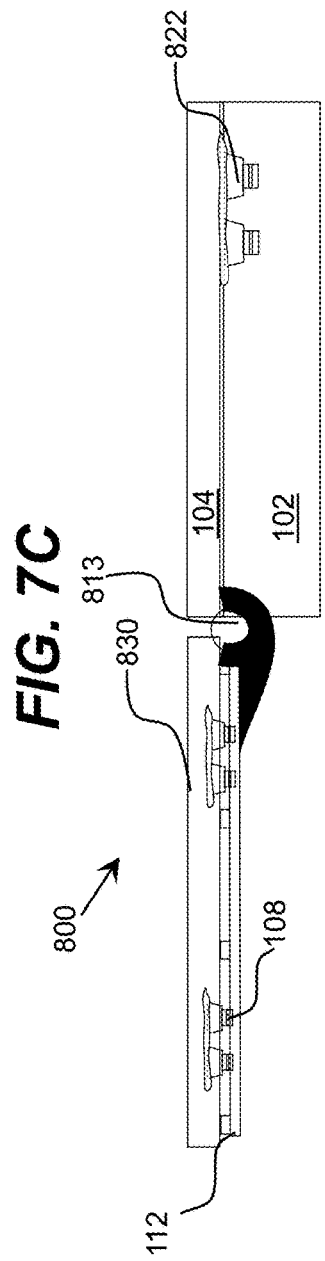

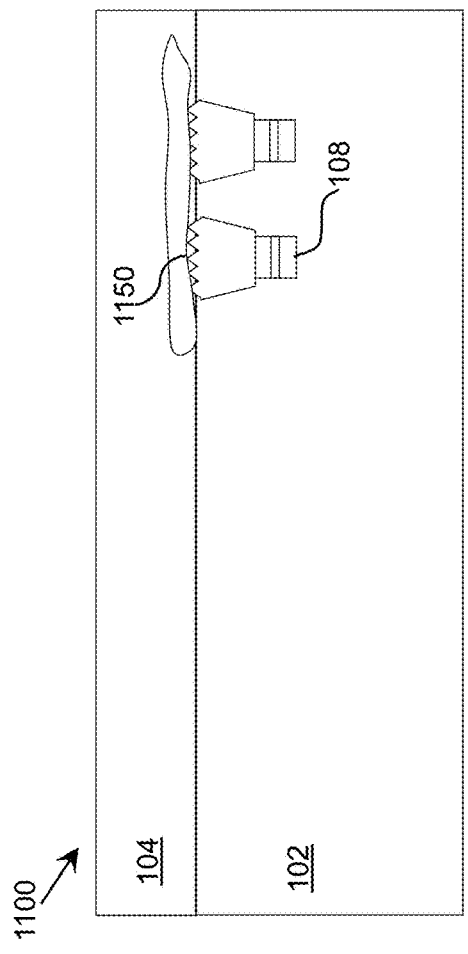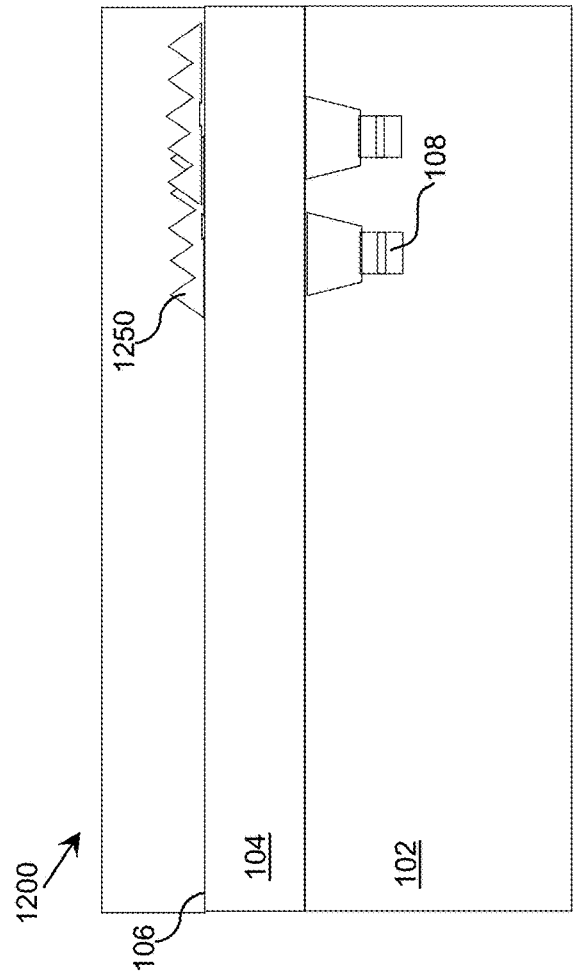

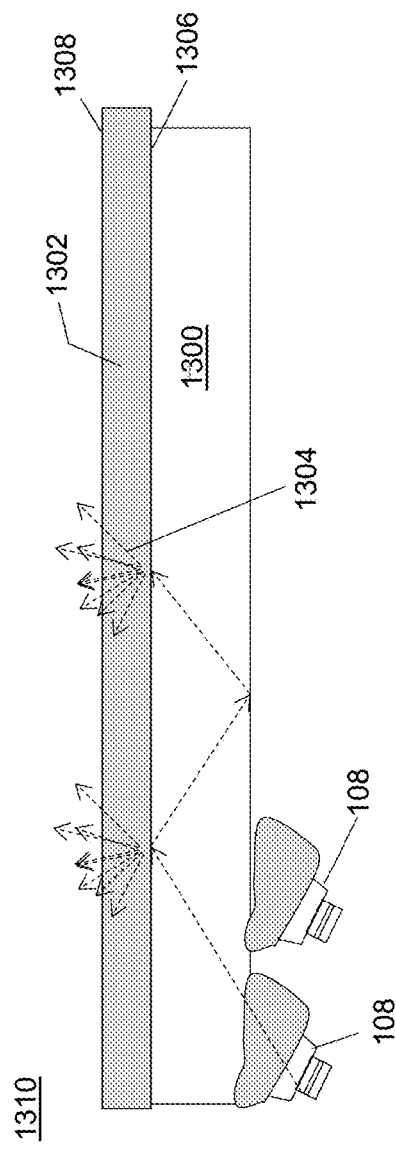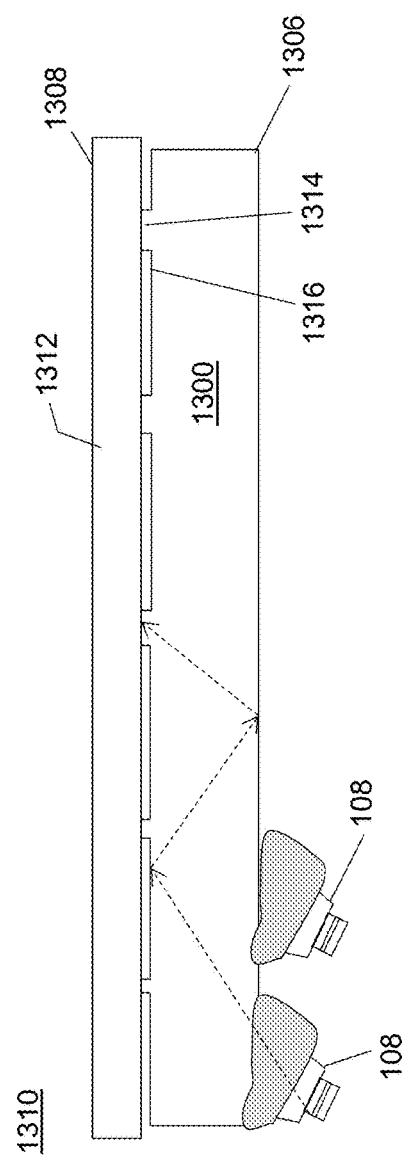

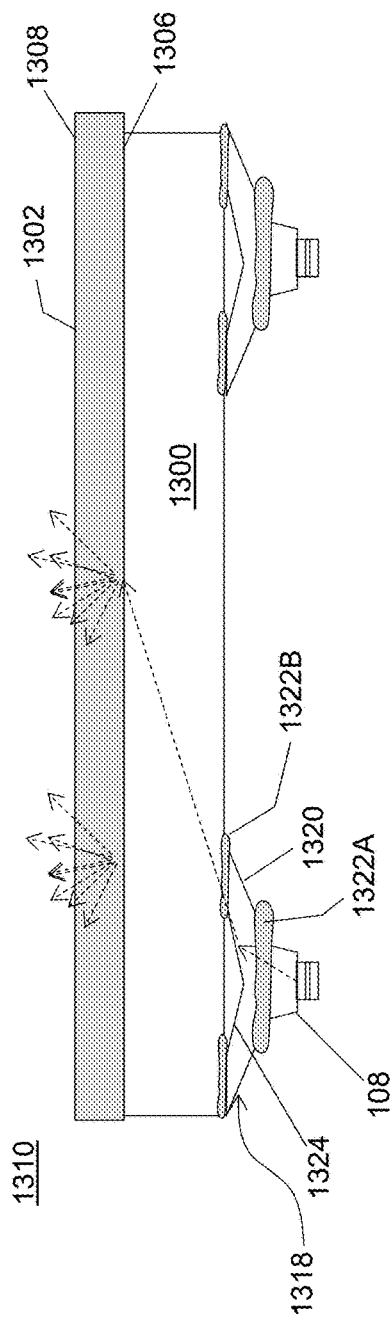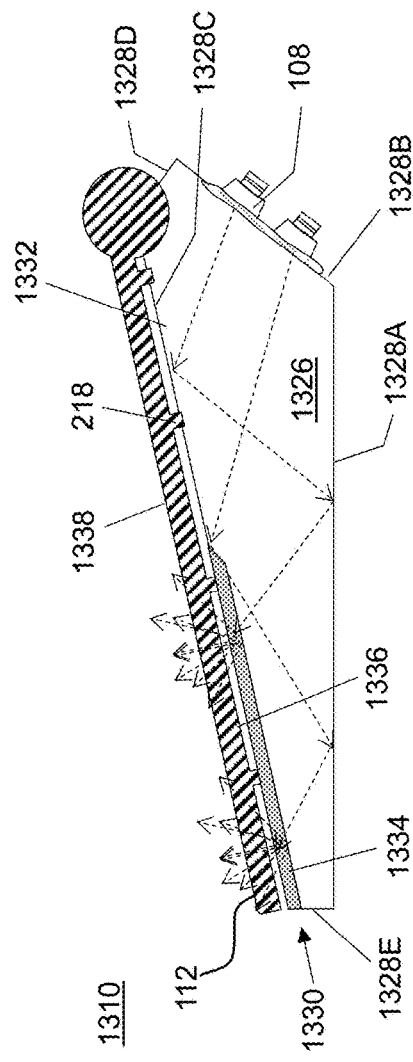

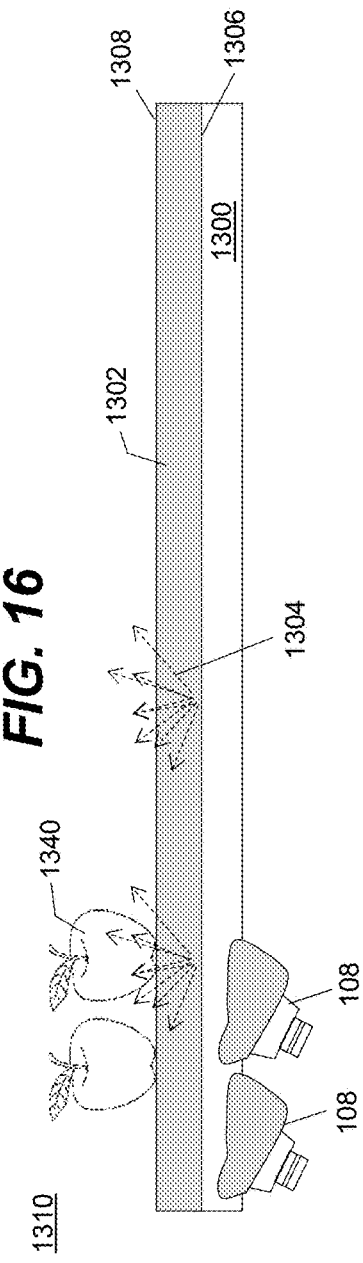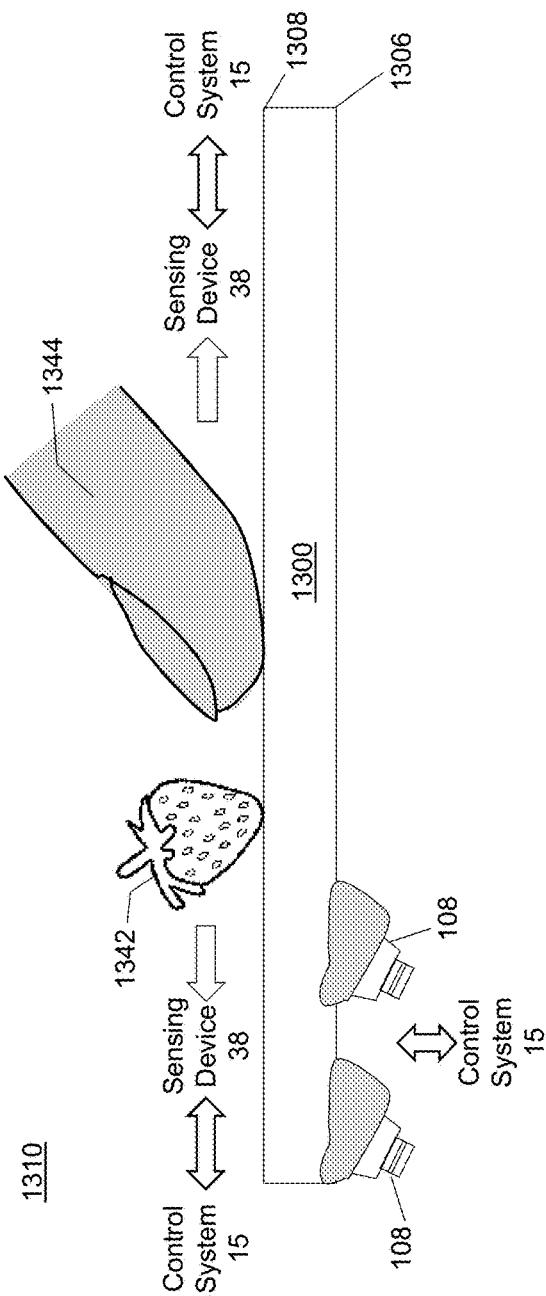

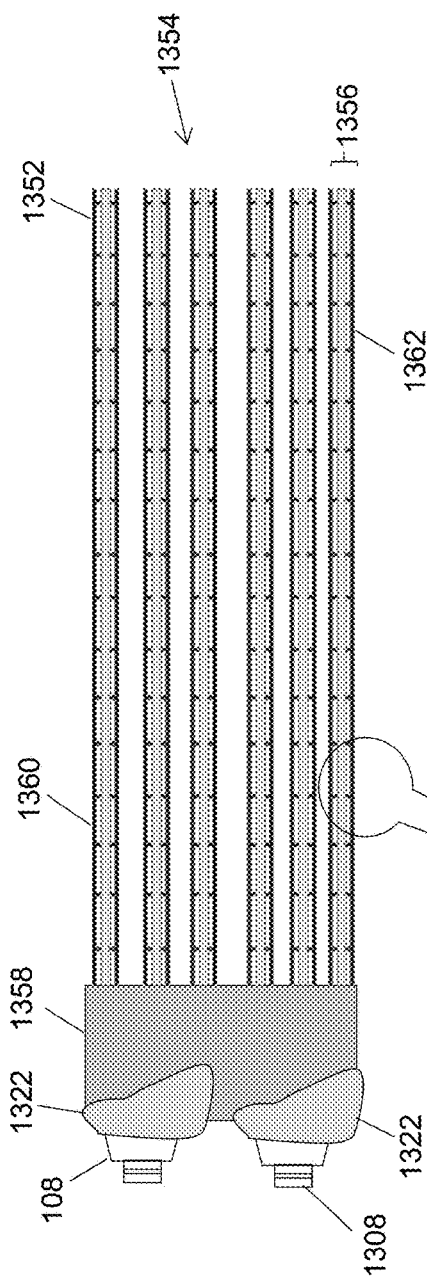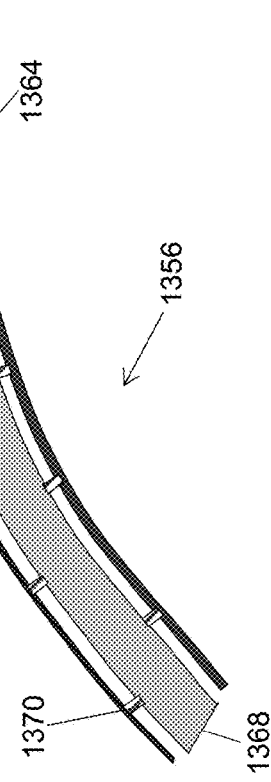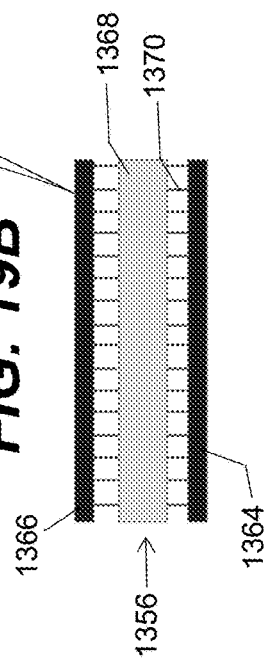

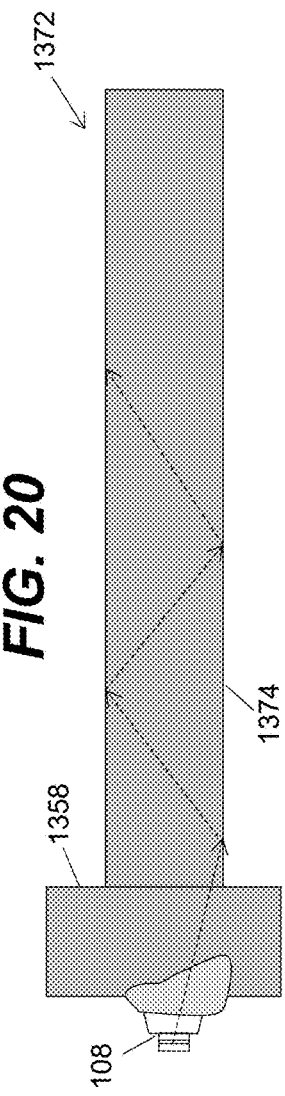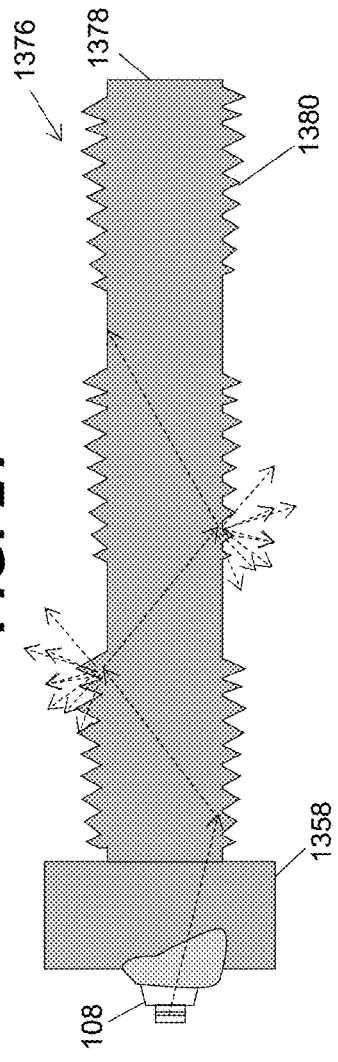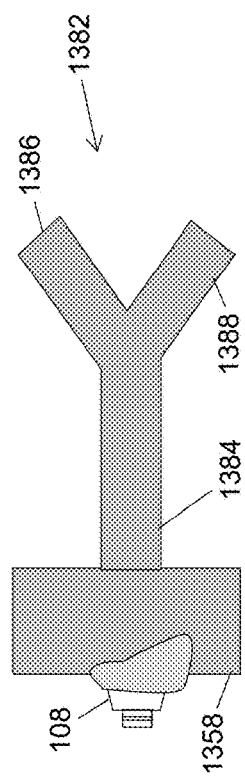

ULTRAVIOLET TRANSPARENT STRUCTURE FOR ULTRAVIOLET ILLUMINATION USING SCATTERED AND FOCUSED RADIATION

REFERENCE TO RELATED APPLICATIONS

The current application is a continuation-in-part of U.S. patent application Ser. No. 15/911,698, filed on 5 Mar. 2018, which is a continuation of U.S. patent application Ser. No. 15/015,539, filed on 4 Feb. 2016, now U.S. Pat. No. 9,907,869, which is a continuation of U.S. patent application Ser. No. 14/640,051, filed on 6 Mar. 2015, now U.S. Pat. No. 9,339,571, which claims the benefit of U.S. Provisional Application No. 61/949,650, filed on 7 Mar. 2014, each of which is hereby incorporated by reference. Aspects of the invention are related to U.S. patent application Ser. No. 13/517,711, filed on 14 Jun. 2012, now U.S. Pat. No. 9,142,741, which is hereby incorporated by reference.

TECHNICAL FIELD

The disclosure relates generally to ultraviolet illumination, and more particularly, to a solution for disinfecting the surface of an item using ultraviolet radiation.

BACKGROUND ART

Ultraviolet (UV) radiation has been utilized to sanitize different devices. For example, there is an approach for sanitizing toothbrushes using UV light. This approach relies on a UV lamp of low intensity for emitting UV radiation in the 200 to 300 nanometer wavelength range, as well as some radiation in the visible range above 300 nanometers and in the ozone producing range below 200 nanometers.

There are currently a number of UV devices available to sterilize mobile phones, such as the UV Sterilizer for the iPhone® from Sinco-Electronic Gifts Co. This UV Sterilizer is a desktop unit. A user places his/her phone into the sterilizer for approximately five minutes. The device turns a blue light emitting diode (LED) on to indicate the start of the sterilization process. Once the blue LED turns off, the sterilization process is complete. Many of such devices utilize mercury lamps to generate the ultraviolet light. However, UV LEDs have been proposed for use in many disinfection-related applications.

SUMMARY OF THE INVENTION

Aspects of the invention provide a solution for disinfecting the surface of a screen of an item using ultraviolet radiation. An embodiment of the solution can include an electronic device including a screen utilized by a user of the electronic device. The screen can be an ultraviolet transparent screen that covers at least some of the internal portion of the electronic device and a set of ultraviolet radiation sources can be located adjacent to the transparent screen. The set of ultraviolet radiation sources can be configured to generate ultraviolet radiation directed towards an external surface of the ultraviolet transparent screen. The electronic device can further include a monitoring and control system, which can manage the ultraviolet radiation generation by monitoring a set of attributes relating to the external surface of the screen and controlling, based on the monitoring, ultraviolet radiation directed at the external surface of the screen.

A first aspect of the invention provides an apparatus comprising: an ultraviolet transparent screen, wherein an external surface of the ultraviolet transparent screen is accessible to a user of the apparatus; a set of ultraviolet radiation sources located adjacent to at least one of: an internal surface or a side of the transparent screen, the set of ultraviolet radiation sources configured to generate ultraviolet radiation directed towards the external surface of the ultraviolet transparent screen; and a monitoring and control system located in an internal portion of the apparatus for managing the ultraviolet radiation by performing a method comprising: monitoring a set of attributes relating to the external surface of the ultraviolet transparent screen; and controlling, based on the monitoring, the ultraviolet radiation directed at the external surface of the ultraviolet transparent screen.

A second aspect of the invention provides an electronic device comprising: an internal portion for containing electronic components of the electronic device; an ultraviolet transparent screen covering at least a portion of the internal portion; a set of ultraviolet radiation sources adjacent to the transparent screen, the set of ultraviolet radiation sources configured to generate ultraviolet radiation to disinfect an external surface of the ultraviolet transparent screen; a cover configured to removably cover the external surface of the ultraviolet transparent screen; and a monitoring and control system for managing the set of ultraviolet radiation sources by performing a method comprising: monitoring a plurality of attributes for the cover and the external surface of the ultraviolet transparent screen; and controlling, based on the monitoring, the ultraviolet radiation directed at the external surface of the ultraviolet transparent screen.

A third aspect of the invention provides a device comprising: an internal portion containing a set of electronic components of the device; an ultraviolet transparent screen covering at least a portion of the internal portion; a set of ultraviolet radiation sources epitaxially grown on an internal surface of the ultraviolet transparent screen, the set of ultraviolet radiation sources configured to generate ultraviolet radiation directed towards an external surface of the ultraviolet transparent screen; and a cover configured to removably cover the ultraviolet transparent screen.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 1A-1B show cross-sectional views of an illustrative device according to an embodiment.

FIG. 3 shows an illustrative system according to an embodiment.

FIGS. 5A-5B show cross-sectional views of an illustrative device according to an embodiment.

FIG. 6 shows a cross-sectional view of an illustrative device according to an embodiment.

FIGS. 7A-7C show cross-sectional views of an illustrative device according to an embodiment.

FIGS. 11A-11B show cross-sectional views of an illustrative device according to an embodiment.

FIG. 12 shows a schematic of an ultraviolet transparent structure having an ultraviolet diffusive layer configured for irradiation by a set of ultraviolet radiation sources according to an embodiment.

FIG. 13 shows a schematic of an ultraviolet transparent structure having an ultraviolet diffusive layer with protrusions configured for irradiation by a set of ultraviolet radiation sources according to an embodiment.

FIG. 14 shows a schematic of an ultraviolet transparent structure having an ultraviolet diffusive layer irradiated by a set of ultraviolet radiation sources with at least one of the sources optically coupled to the structure with an optical element according to an embodiment.

FIG. 15 shows a schematic of an ultraviolet transparent structure having a prismatic shape with a partially reflective and partially transmissive layer and a cover placed over one of the non-parallel surfaces of the structure according to an embodiment.

FIG. 16 shows a schematic of items placed on the ultraviolet transparent structure depicted in FIG. 12 with the set of ultraviolet radiation sources used to disinfect the items according to an embodiment.

FIG. 17 shows a schematic illustrating an ultraviolet transparent structure operating in conjunction with at least one sensing device and a control system to irradiate an item according to an embodiment.

FIGS. 19A-19C show schematic views of an ultraviolet transparent structure having an waveguiding component with a set of individual waveguiding components each configured to waveguide a segment of ultraviolet radiation according to an embodiment.

FIG. 20 shows a schematic of a waveguiding component having an elongated body that can be utilized with an ultraviolet transparent structure according to an embodiment.

FIG. 21 shows a schematic of a waveguiding component having an elongated body with roughness elements that can be utilized with an ultraviolet transparent structure according to an embodiment.

FIG. 22 shows a schematic of a waveguiding component having a main waveguiding body and at least two waveguiding branching members each emanating from the main waveguiding body that can be utilized with an ultraviolet transparent structure according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 2:
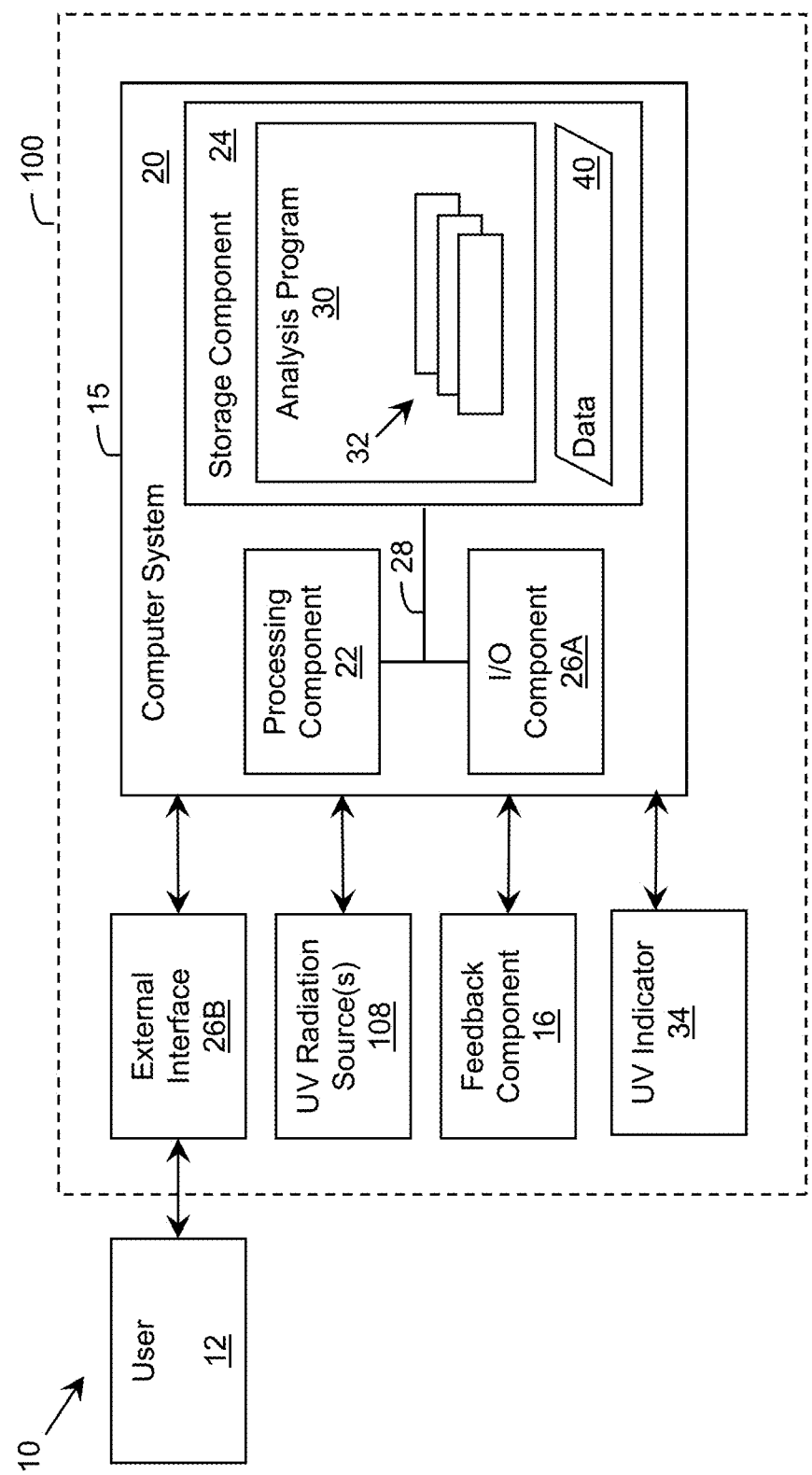
FIG. 2 shows an illustrative environment according to an embodiment.

As indicated above, aspects of the invention provide a solution for disinfecting a screen of an item using ultraviolet radiation. An embodiment provides an electronic device including a screen utilized by a user of the electronic device. The screen can be an ultraviolet transparent screen that covers at least some of the internal portion of the electronic device and a set of ultraviolet radiation sources can be located adjacent to the transparent screen. The set of ultraviolet radiation sources can be configured to generate ultraviolet radiation directed towards an external surface of the ultraviolet transparent screen. The electronic device can further include a monitoring and control system, which can manage the ultraviolet radiation generation by monitoring a set of attributes relating to the external surface of the screen and controlling, based on the monitoring, the ultraviolet radiation directed at the external surface of the screen.

In general, ultraviolet (UV) light is classified into three wavelength ranges: UV-C, from about 200 nanometers (nm) to about 290 nm; UV-B, from about 290 nm to about 315 nm; and UV-A, from about 315 nm to about 420 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through. In an embodiment, the ultraviolet transparent structure is formed of a material and has a thickness, which allows at least ten percent of the ultraviolet radiation to pass there through at a normal incidence to an interface of the material/structure. As used herein, unless otherwise noted, the term "set" means one or more (i.e., at least one) and the phrase "any solution" means any now known or later developed solution.

Furthermore, as used herein, the term "disinfection" and its related terms means treating a device and/or item so that it includes a sufficiently low number of contaminants (e.g., chemical) and microorganisms (e.g., virus, bacteria, and/or the like) so that the device and/or item can be handled as part of a desired human interaction with no or no reasonable risk for the transmission of a disease or other harm to the human. For example, disinfection of the device and/or item means that the device and/or item has a sufficiently low level of active microorganisms and/or concentration of other contaminants that a typical human can interact with the device and/or item without suffering adverse effects from the microorganisms and/or contaminants present on the device and/or item. In addition, disinfection can include sterilization. As used herein, the term "sterilization" and its related terms means neutralizing an ability of a microorganism to reproduce, which may be accomplished without physically destroying the microorganism. In this example, a level of microorganisms present on the device and/or item cannot increase to a dangerous level and will eventually be reduced, since the replication ability has been neutralized. A target level of microorganisms and/or contaminants can be defined, for example, by a standards setting organization, such as a governmental organization.

Turning to the drawings, FIG. 1A shows a cross-sectional view of a device 100 according to an embodiment. The device 100 can include any type of handheld electronic gadget, such as a mobile phone, a tablet, a laptop, and/or the like. In this case, the device 100 includes an internal portion 102 for containing electronic components of the electronic gadget. An ultraviolet transparent screen 104 is located on top of the internal portion 102 and can be formed of any ultraviolet transparent material, such as fused silica, sapphire, quartz, an ultraviolet transparent polymer, and/or the like. In an embodiment, the transparent screen 104 can include at least one ultraviolet transparent polymer, such as, for example, fluorinated ethylene propylene (FEP), fluorinated ethylene propylene co-polymer (EFEP), polyactic acid (PLA), low-density polyethylene (LDPE), and/or the like. In particular, these materials are sufficiently transparent to transmit ultraviolet radiation of certain wavelengths. The transparent screen 104 includes a top surface 106 which is accessible to a user of the electronic gadget and would require disinfection. In an embodiment, the ultraviolet transparent screen 104 is formed of a material that is transparent and includes a refractive index that is similar to sapphire, wherein similar is within approximately 30% of the refractive index of sapphire. In an embodiment, the ultraviolet transparent screen 104 can be discontinuous and cover between approximately 5% to approximately 90% of the lateral area of the internal portion 102 of the device 100.

The device 100 can include a set of ultraviolet radiation sources 108 located in the internal portion 102 of the device 100, which can be placed adjacent to the ultraviolet transparent screen 104. In FIG. 1A, only one ultraviolet radiation source 108 is shown for illustrative purposes and it is understood that any number of ultraviolet radiation sources 108 may be located within the device 100. For example, in FIG. 1B, the device 100 is shown including a first ultraviolet radiation source 108A and a second ultraviolet radiation source 108B. It is understood that certain layers (e.g., layer 110) can be omitted from the device 100 (e.g., in FIG. 1B). The set of ultraviolet radiation sources 108 can comprise any combination of one or more ultraviolet radiation emitters. For example, the set of ultraviolet radiation sources 108 can include a high intensity ultraviolet lamp (e.g., a high intensity mercury lamp), a discharge lamp, an ultraviolet light emitting diode (LED), super luminescent LEDs, laser diodes, and/or the like. In an embodiment, the set of ultraviolet radiation sources 108 includes a set of light emitting diodes manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the set of ultraviolet radiation sources 108 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, towards the transparent screen 104. Illustrative wave guiding structures include, but are not limited to, a plurality of ultraviolet fibers, each of which terminates at an opening, a diffuser, and/or the like.

As illustrated in FIG. 1A, a layer 110 including a refractive index that is lower than the refractive index of the ultraviolet transparent screen 104 can be located on top of the ultraviolet transparent screen 104. In an embodiment, the refractive indexes are selected to increase an amount of total internal reflection (TIR) of the ultraviolet radiation that occurs at a boundary between the layer 110 and the ultraviolet transparent screen 104. For example, in an embodiment, the layer 110 can include ambient air. The device 100 can further include a cover 112 located on top of the layer 110. The cover 112 can include a reflective surface 114, which is configured to reflect ultraviolet radiation in a direction of the top surface 106 of the transparent screen 104. The reflective surface 114 can include a material that is at least 50% reflective to radiation at a normal incidence. In an embodiment, the reflective surface 114 is at least 70% reflective. The reflective surface 114 can be formed of any type of reflective material. For example, illustrative ultraviolet reflective materials include: polished aluminum, a highly ultraviolet reflective expanding polytetrafluoroethylene (ePTFE) membrane (e.g., GORE® DRP® Diffuse Reflector Material), a fluoropolymer (e.g., Spectralon® by Labsphere, Inc.), and/or the like. The cover 112 also can include a layer of material that has antibacterial properties, such as titanium dioxide ($TiO_2$), which can assist in sterilization and disinfection and is activated by light.

FIGS. 1A and 1B show illustrative examples of ultraviolet radiation emitted from the set of ultraviolet radiation sources 108. The ultraviolet radiation can be transmitted through the transparent screen 104 and reflected at the top surface 106 of the transparent screen 104 by total internal reflection (TIR) and/or off the reflective surface 114 in order to disinfect the top surface 106 of the transparent screen 104. The ultraviolet radiation can continue to be transmitted through the transparent screen 104 and reflect off a surface of the internal portion 102, so that ultraviolet radiation is recycled within the device 100.

Turning now to FIG. 2, an illustrative ultraviolet radiation system 10 according to an embodiment is shown. In this case, the system 10 includes a monitoring and/or control system 15 incorporated in the device 100, which is shown implemented as a computer system 20 including an analysis program 30, which makes the computer system 20 operable to manage an ultraviolet radiation source 108 by performing a process described herein. In particular, the analysis program 30 can enable the computer system 20 to operate the ultraviolet radiation source(s) 108 to generate and direct ultraviolet radiation toward the top surface 106 of the transparent screen 104 of the device 100 (FIG. 1A) and process data corresponding to one or more attributes regarding the device 100, which is acquired by a feedback component 16, and/or an ultraviolet radiation history stored as device data 40. While a single ultraviolet radiation source 108 is shown in this figure, it is understood that the device 100 can include any number of ultraviolet radiation sources 108, the operation of which the computer system 20 can separately manage using a process described herein. In the case of more than one ultraviolet radiation source 108 (e.g., as shown in FIG. 1B), it is understood that the computer system 20 can individually control each ultraviolet radiation source 108 and/or control two or more of the ultraviolet radiation sources 108 as a group. Furthermore, the ultraviolet radiation sources can emit ultraviolet radiation of substantially the same wavelength or of multiple distinct wavelengths.

In an embodiment, during an initial period of operation (e.g., while the cover 112 is placed over the transparent screen 104 (FIG. 1A), and/or the like), the computer system 20 can acquire data from the feedback component 16 regarding one or more attributes of the device 100 and generate data 40 for further processing. The data 40 can include a presence of biological activity (e.g., microorganisms, viruses, bacteria, and/or the like) on the top surface 106, a frequency of usage of the electronic gadget of the device 100, a disinfection schedule history for the device 100, an amount of radiation (e.g., ultraviolet, infrared, visible, and/or microwave), and/or the like. The computer system 20 can use the data 40 to control one or more aspects of the ultraviolet radiation generated by the ultraviolet radiation source(s) 108.

Furthermore, one or more aspects of the operation of the ultraviolet radiation source 108 can be controlled by a user 12 via an external interface component 26B. The external interface component 26B can be located on the top surface 106 (FIG. 1A) and allow the user 12 to choose when to turn on the ultraviolet radiation source 108. However, it is understood that, in order to turn on the ultraviolet radiation source 108, the computer system 20 can first determine that the cover 112 is over the remaining portions of the device 100 to avoid harming the user 12, e.g., using data acquired by the feedback component 16. The external interface component 26B can include a touch screen that can selectively display user interface controls, such as control dials, which can enable the user 12 to adjust one or more of: an intensity, scheduling, and/or other operational properties of the set of ultraviolet radiation sources 108. In an embodiment, the external interface component 26B can include a keyboard, a plurality of buttons, a joystick-like control mechanism, and/or the like, which can enable the user 12 to control one or more aspects of the operation of the set of ultraviolet radiation sources 108.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 12 to interact with the computer system 20 and/or one or more communications devices to enable a system user 12 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 12 to interact with the analysis program 30. Furthermore, the analysis program 30 can manage (e.g., store, retrieve, create, manipulate, organize, present, etc.) the data, such as data 40, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 15 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 15.

Regardless, when the computer system 20 includes multiple computing devices, the computing devices can communicate over any type of communications link. Furthermore, while performing a process described herein, the computer system 20 can communicate with one or more other computer systems, such as the user 12, using any type of communications link. In either case, the communications link can comprise any combination of various types of wired and/or wireless links; comprise any combination of one or more types of networks; and/or utilize any combination of various types of transmission techniques and protocols.

The system 10 also can include an ultraviolet radiation indicator 34 (e.g., an LED), which can be operated by the computer system 20 to indicate when ultraviolet radiation is being generated within the device 100. The ultraviolet radiation indicator 34 can include one or more LEDs for emitting a visual light for the user 12. In another embodiment, the indicator 34 can be an alarm (e.g., an auditory signal) for signaling that ultraviolet radiation is being generated.

Turning now to FIG. 3, an illustrative system including an ultraviolet radiation system 10 for disinfecting the transparent screen 104 (FIG. 1A) is shown. The computer system 20 is configured to control the ultraviolet radiation source 108 to direct ultraviolet radiation 13 at the transparent screen 104 as described herein. The feedback component 16 is configured to acquire data used by the computer system 20 to monitor a set of attributes regarding the device 100 over a period of time. As illustrated, the feedback component 16 can include a plurality of sensing devices 38, each of which can acquire data used by the computer system 20 to monitor the set of attributes.

It is understood that the set of attributes for the device 100 can include any combination of one or more of: a frequency of the usage of the device 100, a presence of biological activity on the transparent screen 104, a usage of the device 100, a disinfection schedule history for the device 100, and/or the like. In the case of determining usage details for the device 10, a sensing device 38 can include a sensor and/or a switch to sense that the cover 112 is over the remaining portion of the device 100. If the sensing device 38 senses that the cover 112 is not over the remaining portion of the device 100, the computer system 20 can either terminate the ultraviolet radiation 13 generated by set of ultraviolet radiation sources 108 and/or fail to turn on the set of ultraviolet radiation sources 108.

In the case of determining a presence of biological activity on the transparent screen 104 of the device 100, the sensing devices 38 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the sensing device 38 can determine information on the variation of the biological activity over time, such as a growth rate, a rate with which an area including the biological activity is spreading, and/or the like. In an embodiment, a set of biological activity dynamics are related to various attributes of bacteria and/or virus activity present on the transparent screen 104, including, for example, the presence of detectable bacteria and/or virus activity, measured bacteria and/or virus population/concentration time dynamics, growth phase, and/or the like.

In an embodiment, to determine the presence of biological activity on the transparent screen 104, the sensing devices 38 include at least one of a visual camera or a chemical sensor. The visual camera can acquire visual data (e.g., visual, electronic, and/or the like) used to monitor the transparent screen 104, while the chemical sensor can acquire chemical data (e.g., chemical, electronic, and/or the like) used to monitor the transparent screen 104. For example, when the computer system 20 is operating the ultraviolet radiation source 108, a visual camera and/or a chemical sensing device monitoring the transparent screen 104 may be operated to detect the presence of microorganisms. In a specific embodiment, the visual camera comprises a fluorescent optical camera that can detect bacteria and/or viruses that become fluorescent under ultraviolet radiation. However, it is understood that a visual camera and a chemical sensor are only illustrative of various types of sensors that can be implemented. For example, the sensing devices 38 can include one or more mechanical sensors (including piezoelectric sensors, various membranes, cantilevers, a microelectromechanical sensor or MEMS, a nanomechanical sensor, and/or the like), which can be configured to acquire any of various types of data regarding the transparent screen 104.

The computer system 20 can be configured to control and adjust a direction, an intensity, a pattern, and/or a spectral power (e.g., wavelength) of the set of ultraviolet radiation sources 108, based on data received from the feedback component 16. The computer system 20 can control and adjust each property of the set of ultraviolet radiation sources 108 independently. For example, the computer system 20 can adjust the intensity, time duration, and/or time scheduling (e.g., including duration (e.g., exposure/illumination time)), duty cycle, time between exposures/illuminations, and/or the like) of the ultraviolet radiation source 108 for a given wavelength. Each of the properties of the ultraviolet radiation source 108 can be adjustable and controlled by the computer system 20 according to data provided by the feedback component 16.

For example, the computer system 20 can be configured to adjust the direction of the ultraviolet radiation according to a location of the biological activity detected on the transparent screen 104 by the sensing device(s) 38 using any solution. The computer system 20 can be configured to utilize a target timing, intensity, and/or spectral power of the ultraviolet radiation 13 according to a type of biological activity. That is, the sensing devices 38 can sense locations of higher levels of biological activity on the transparent screen 104, and the ultraviolet radiation source 108 can be configured by the computer system 20 to direct higher doses (by increasing intensity or exposure) of ultraviolet radiation at the locations with higher levels of biological activity (e.g., non-uniform ultraviolet radiation).

The sensing devices 38 can also sense whether or not the cover 112 (FIG. 1A) is on and covering the remaining portion of the device 100. In response to detection of the cover 112 being present on the remaining portion of the device 100, the computer system 20 can be configured to automatically turn on the ultraviolet radiation 13. In one embodiment, the computer system 20 can be configured to set a periodic or an aperiodic schedule for the ultraviolet radiation when the cover 112 is in place. This (periodic or aperiodic) schedule can be interrupted when the sensing device 38 senses that the cover 112 is removed from the device 100 and the computer system 20 can be configured to turn off the ultraviolet radiation. In this case, the schedule (periodic or aperiodic) can be resumed once the sensing device 38 senses the cover 112 is in place.

The sensing device 38 can also include a radiation detector for detecting an amount of radiation that the top surface 106 is exposed to. The radiation can include any type of radiation, including, for example, ultraviolet, visible, infrared, microwave, and/or the like. The amount of radiation that the top surface 724 is exposed to can be used by the computer system 20 to determine if any additional radiation is required to disinfect the top surface 106.

It is understood that the system 10 may include a power component 17 that is implemented to supply power to one or more of the various components of system 10, such as the ultraviolet radiation source(s) 108, feedback component 16, computer system 20, and/or the like. For example, the device 100 (FIG. 1A) may comprise a power source that is insufficient to operate the various devices of system 10 in addition to maintaining sufficient power to continue one or more aspects of the operation of the device 100. Regardless, the power component 17 can be utilized to operate system 10. The power component 17 can be embedded in the internal portion 102 (FIG. 1A) of the device 100 along with the set of ultraviolet radiation sources 108. The power component 17 can comprise any source of power including, but not limited to, a battery set, a solar cell, and/or the like. For example, the power component 17 can include any of various types of rechargeable batteries (e.g., lithium ion, nickel-cadmium, and/or the like). The power component 17 can be configured for operation of high efficiency direct current (DC) step-up/boost converters. In an embodiment, the power component (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a Universal Serial Bus (USB) connection. In another embodiment, heat from a user provides power to the power component 17. In an embodiment, the power component 17 and/or other electronic components (e.g., computer system 20, feedback component 16, and/or the like) can be grown and monolithically integrated on a sapphire surface of the internal portion 102 (FIG. 1A).

Figure 4A:
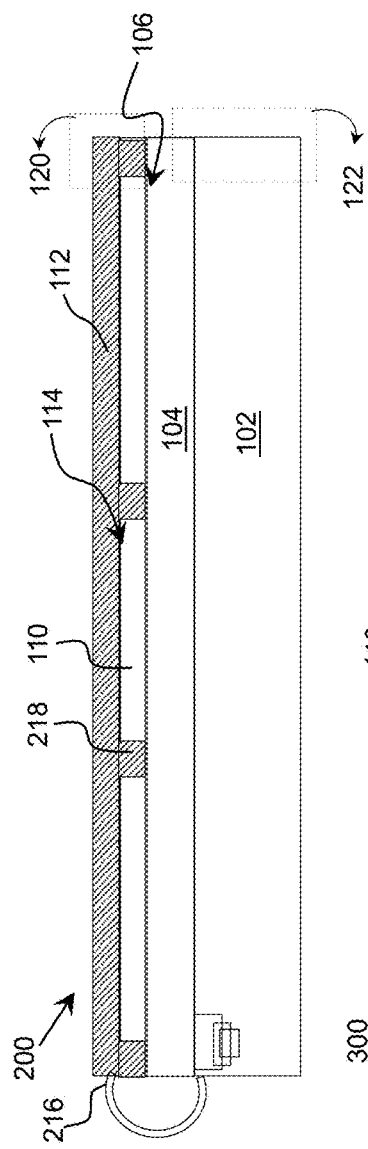
FIGS. 4A-4C show cross-sectional views of an illustrative device according to an embodiment.
Figure 4B:
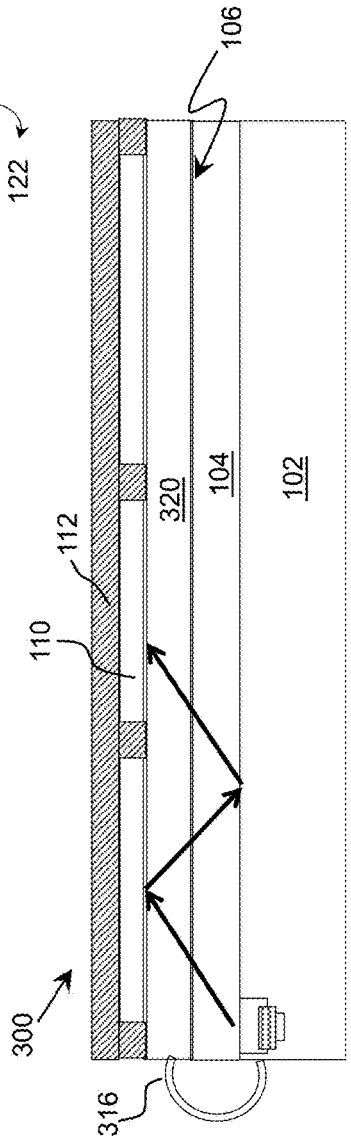
Figure 4C:
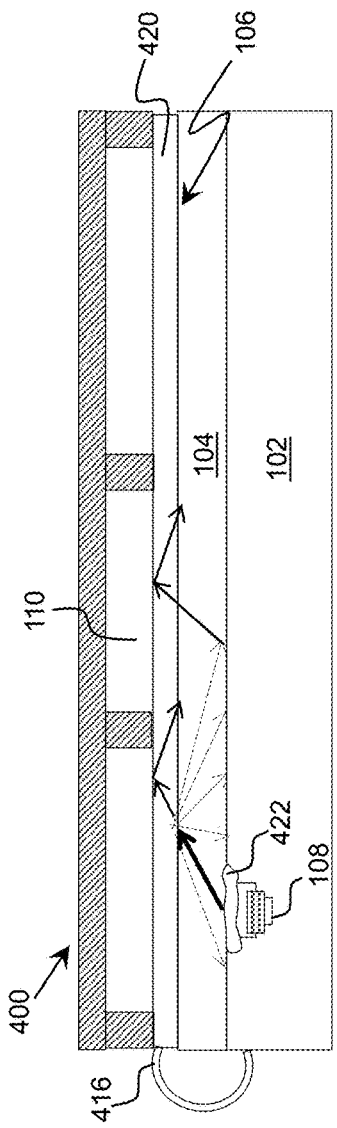

Turning now to FIGS. 4A-4C, cross-sectional views of illustrative devices 200, 300, 400 according to embodiments are shown. In FIG. 4A, the device 200 is similar to the device 100 shown in FIG. 1A. However, the device 200 can include a hinge 216 coupled to the cover 112 and a portion of the device 200. The portion can be either the internal portion 102, the transparent screen 104, and/or the like. The hinge 216 is used to open and close the cover 112. The hinge 216 can enable movement of the cover 112 and a remaining portion of the device 200 away from one another in the direction of arrows 120, 122. It is understood that the hinge 216 shown in FIGS. 4A-4C is only illustrative of various mechanisms that can be utilized for opening and closing the cover 112. For example, the cover 112 can slide on and off the device 200 using a track, be magnetically attached to the device 100, and/or the like. In the embodiment where the cover 112 can slide on and off of the device 200, the sliding motion can result in the top surface 106 of the ultraviolet transparent screen 104 being wiped. In this embodiment, the reflective surface 114 (FIG. 1A) of the cover 112 can include a material for wiping the top surface 106 of the ultraviolet transparent screen 104. The cover 112 can also contain an antibacterial liquid that is released during the sliding/wiping motion of the cover 112. Examples of antibacterial liquids include alcohols, triclosan, triclocarban, chloroxylenol and/or the like. The cover 112 can include a plurality of fins 218 of substantially the same height and width. The plurality of fins 218 extend from the cover 112 into the layer 110 (e.g., air) and touch the top surface 106 of the transparent screen 104. The plurality of fins 218 can provide a boundary between the cover 112 and the transparent screen 104.

In FIG. 4B, the device 300 can include an additional ultraviolet transparent layer 320 located above the transparent screen 104. The ultraviolet radiation generated by the ultraviolet radiation source 108 can transmit through both the transparent screen 104 and the additional ultraviolet transparent layer 320. A difference in the refractive indices at the interface of the layer 110 (e.g., air) and the additional ultraviolet transparent layer 320 can reflect the ultraviolet radiation back towards the transparent screen 104, as shown by the arrows in FIG. 4B. In this manner, the top surface 106 of the transparent screen 104 can be disinfected. In an embodiment, the additional ultraviolet transparent layer 320 can be formed of an ultraviolet transparent material with a refractive index that is higher than the refractive index of the layer 110. The refractive index of the additional ultraviolet transparent layer 320 can be substantially similar or the same as the refractive index of the transparent screen 104. For example, when the layer 100 includes air, the additional ultraviolet transparent layer 320 and/or the transparent screen 104 can be formed of fused silica, sapphire, and/or the like. In this embodiment, the hinge 316 (or other mechanism) can be coupled to the additional ultraviolet transparent layer 320, instead of the cover 112 as shown in FIG. 4A, so that both the cover 112 and the additional ultraviolet transparent layer 320 are removed or opened by the hinge 316 to enable access to the surface 106 by a user.

In FIG. 4C, the device 400 can include a diffusively reflective layer 420. The diffusively reflective layer 420 can also be partially transmitting. The diffusively reflective layer 420 can include a diffusive reflection of at least approximately 30% of radiation at a normal incidence. The diffusively reflective layer 420 can be formed by an ultraviolet reflective material, including polished aluminum, a highly ultraviolet reflective expanding polytetrafluoroethylene (ePTFE) membrane (e.g., GORE® DRP® Diffuse Reflector Material), a fluoropolymer (e.g., Spectralon® by Labsphere, Inc.), and/or the like. The ultraviolet radiation generated by the ultraviolet radiation source 108 is diffusively reflected by the diffusively reflective layer 420, but can also be partially transmitted by the diffusively reflective layer 420, as shown by the arrows in FIG. 4C. The ultraviolet radiation that is transmitted by the diffusively reflective layer 420 can be reflected by the interface between the layer 110 and the diffusively reflective layer 420, so that the top surface 106 of the transparent screen 104 is disinfected.

An ultraviolet radiation source 108 can be attached to the device 100 using any known method. For example, the ultraviolet radiation source 108 can be grown on a sapphire substrate through epitaxy and the sapphire substrate can be utilized as the screen of the device 100 as it constitutes a transparent and scratch resistant material. In another embodiment, the ultraviolet radiation source 108 can be attached using ultraviolet transparent glue, such as the glue 422 shown in FIG. 4C. The ultraviolet transparent glue 422 can be formed of an ultraviolet transparent polymer including a high degree (e.g., at least thirty percent) of ultraviolet transparency such as EFEP, and/or the like. In a preferred embodiment the material is at least 50% transparent.

The ultraviolet radiation source(s) 108 can be located adjacent to any layer of the device 100 and emit radiation at any angle. For example, as shown in FIG. 5A, the device 500 includes the ultraviolet radiation source 108 located on a side of the transparent screen 104. The device 500 can also include a reflecting element 524 located on the opposite side of the ultraviolet radiation source 108. The reflecting element 524 can be configured to redirect any ultraviolet radiation back towards the transparent screen 104 to disinfect the top surface 106. In the embodiment shown, the reflecting element 524 includes a parabolic shaped surface for reflecting the ultraviolet radiation. However, this parabolic shape is for illustrative purposes and it is understood that the reflecting element can be any shape. For example, in FIG. 5B, the reflecting element 624 of the device 600 includes a flat surface for reflecting the ultraviolet radiation. In the embodiment shown in FIG. 5B, the device 600 does not need to include the layer 110 (e.g., air), the plurality of fins 518, or the additional ultraviolet transparent layer 520, which are shown in the embodiment of the device 500 in FIG. 5A. However, these features can be included in the embodiment.

The device can also include a set of detectors (e.g., sensors 38 in FIG. 3). As shown in FIG. 6, the device 700 can include the set of detectors 722, which are located beneath the transparent screen 104. The set of detectors 722 can be configured to detect radiation 724 (e.g., ultraviolet, infrared, visible, microwave, and/or the like). The set of detectors 722 can be attached to the device 700 in a method similar to how the set of ultraviolet radiation sources 108 (FIG. 4C) are attached (e.g., grown or glued on the transparent screen 104). As mentioned herein, ultraviolet transparent glue can be used to attach the set of detectors 722 and/or the set of ultraviolet radiation sources to the device. When the cover 112 is in an open position, and the top surface 106 of the transparent screen 104 is exposed, the detectors 722 can detect an amount and/or type of ambient radiation 724 that the top surface 106 is exposed to. As mentioned herein, the amount and/or type of radiation 724 (ambient and/or emitted by ultraviolet radiation sources 108) that the top surface 106 is exposed to can be used by the monitoring and/or control system 15 (FIG. 2) to control the ultraviolet radiation generated by the set of ultraviolet radiation sources.

Turning now to FIGS. 7A-7C, the device 800 can include a second transparent screen 830 to extend the functionality of the device 800. The second transparent screen 830 can be located between the cover 112 and the transparent screen 104. The second transparent screen 830 can be formed of a material that is substantially the same, or identical to, the material of the transparent screen 104. In the embodiment shown in FIG. 7A, the device 800 includes a set of ultraviolet radiation sources 108 that is located next to the transparent screen 104. However, as discussed herein, the set of ultraviolet radiation sources 108 can be positioned in any layer and at any angle within a device. In the embodiment shown in FIGS. 7B and 7C, some or all of the set of ultraviolet radiation sources 108 are located within the second transparent screen 830. Although the set of detectors 822 are only shown in FIGS. 7B and 7C, it is understood that the embodiment shown in FIG. 7A can also include the set of detectors 822. In FIG. 7A, the cover 112 and the second transparent screen 830 are in a closed position via the hinge 813. In FIG. 7B, the cover 112 and the second transparent screen 830 are in a partially opened position via the hinge 813. In FIG. 7C, the cover 112 and the second transparent screen 830 are in an open position via the hinge 813. In this open position, the second transparent screen 830 can be utilized by a user along with the transparent screen 104, e.g., as part of operating the device 800 (e.g., a smartphone, tablet, and/or the like) in its intended manner.

Figure 8:
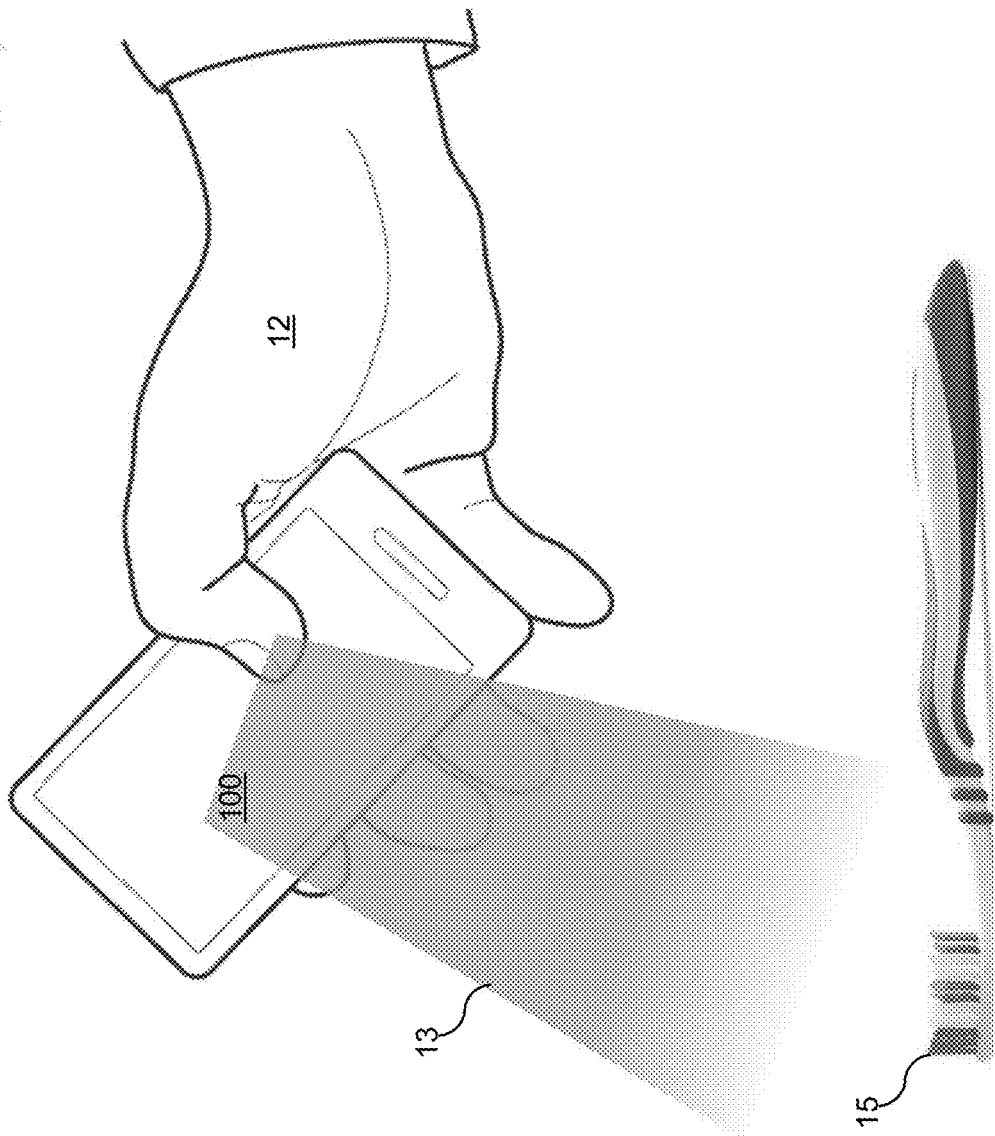
FIG. 8 shows a perspective view of a user implementing an illustrative device as a sterilizing wand according to an embodiment.

In addition to disinfecting a top surface of a device, the ultraviolet radiation system within a device can be used to disinfect other items. For example, as shown in FIG. 8, a user 12 can utilize a device discussed herein, for example, the device 100 shown FIG. 1, to generate ultraviolet radiation 13 directed toward an item 15 in order to disinfect the item 15 (e.g., a toothbrush). In this case, referring to FIG. 3, the computer system 20 can control the set of ultraviolet radiation sources 108 so that when the device 100 is used in this manner, a more focused type of radiation is used so that ultraviolet radiation 13 is only targeted towards the item 15. In contrast, when the device 100 is used to disinfect the top surface 106, a more scattered type of radiation is used so that the top surface 106 is disinfected uniformly and efficiently. In an embodiment, the device 100 can include a first set of ultraviolet radiation sources that are utilized for the focused type of radiation and a second set of ultraviolet radiation sources that are utilized for the scattered type of radiation. Furthermore, the computer system 20 can use data acquired by the feedback component 16 (e.g., visible image data, infrared image data, and/or the like) to ensure that the ultraviolet radiation is being directed onto an object that will not be harmed by the ultraviolet radiation.

Figure 9:
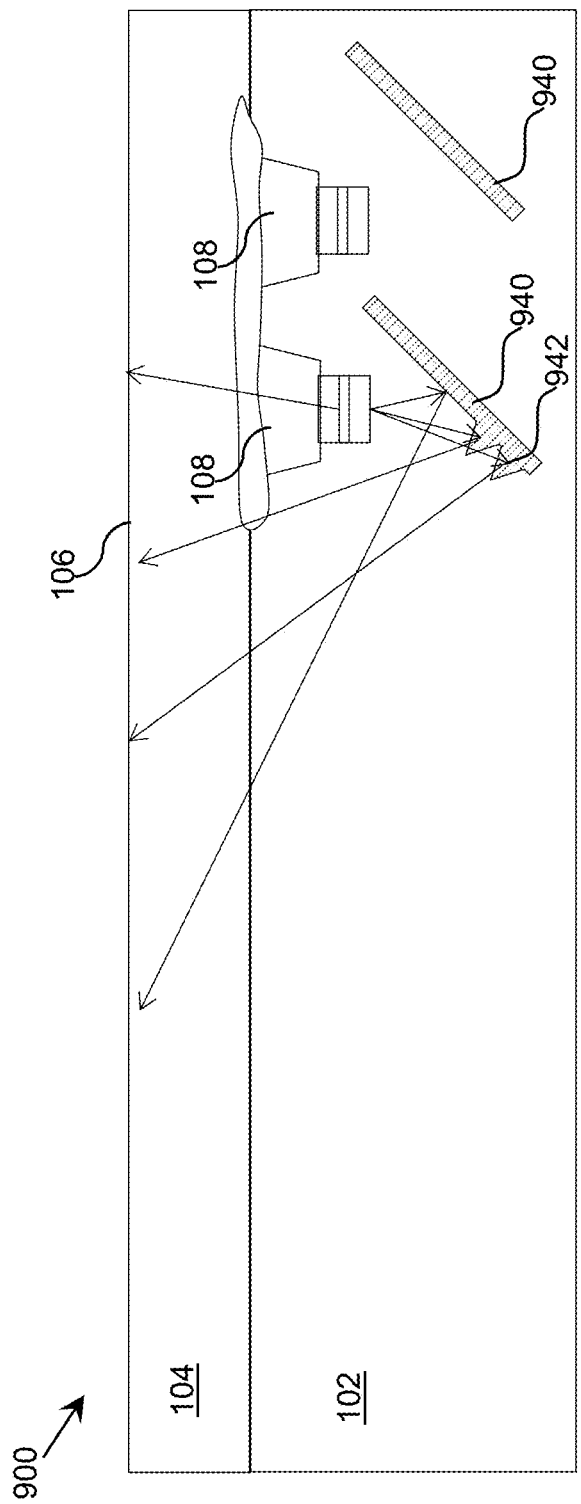
FIG. 9 shows a cross-sectional view of an illustrative device according to an embodiment.

Turning now to FIG. 9, a device 900 can include one or more reflecting elements 940 configured to reflect the ultraviolet radiation towards the top surface 106 of the transparent screen 104. The reflecting element 940 can be formed of any ultraviolet reflecting material, such as polished aluminum, a highly ultraviolet reflective expanding polytetrafluoroethylene (ePTFE) membrane (e.g., GORE® DRP® Diffuse Reflector Material), a fluoropolymer (e.g., Spectralon® by Labsphere, Inc.), and/or the like. In an embodiment, a reflecting element 940 can be located beneath each ultraviolet radiation source 108. In another embodiment, one or more of the reflecting elements 940 can include a set of protrusions 942 to further help in reflecting and/or directing the ultraviolet radiation.

Figure 10:
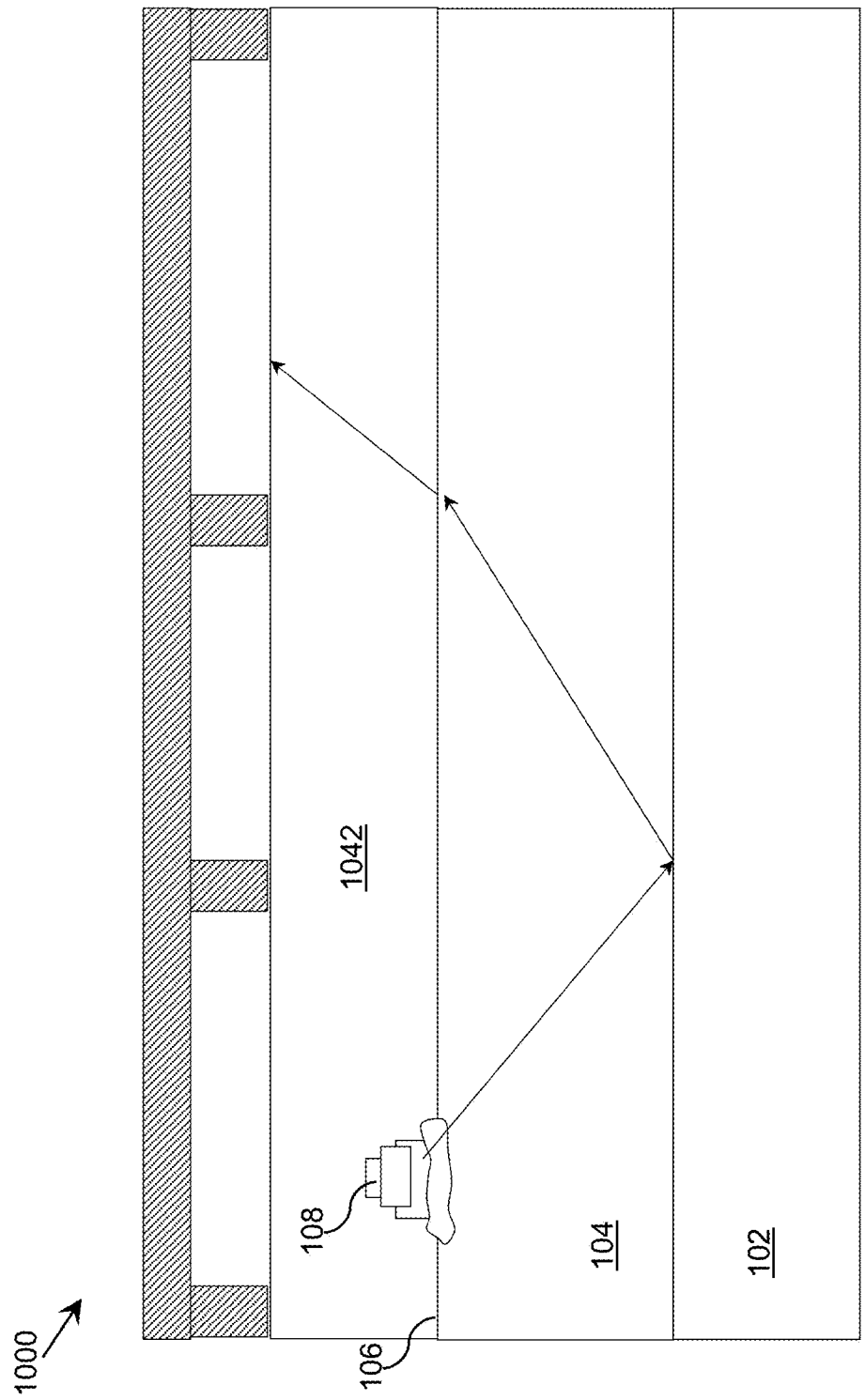
FIG. 10 shows a cross-sectional view of an illustrative device according to an embodiment.

Turning now to FIG. 10, a device 1000 is shown including an ultraviolet transparent protective layer 1042 over the transparent screen 104. In this embodiment, the set of ultraviolet radiation sources 108 can be grown over the top of the transparent screen 104 (e.g., sapphire screen) as long as there is sufficient reflectance at the interface of the transparent screen 104 and the internal portion 102. In an embodiment, the reflectance is at least 20% for sufficient disinfection action. The ultraviolet transparent protective layer 1042 can be formed of an ultraviolet transparent polymer, such as FEP, EFEP, PLA, LDPE, and/or the like. The ultraviolet transparent protective layer 1042 can be provide antireflective and/or screen protection, as well as encapsulating the UV LED source 108.

Turning now to FIGS. 11A and 11B, devices 1100, 1200 can include a roughness component 1150, 1250 configured to improve the light extraction from the set of ultraviolet radiation sources 108. The size of the roughness component 1150, 1250 can be larger or comparable to the wavelength of the ultraviolet radiation generated by the set of ultraviolet radiation sources 108. In FIG. 11A, the roughness component 1150 can be incorporated with the ultraviolet radiation sources 108. For example, a typical ultraviolet radiation device 108 epitaxially grown on a sapphire substrate (e.g., the transparent screen 104) can have a roughness deposited on sapphire surface being a surface opposite to the one where the epitaxial growth has been carried. In FIG. 11B, the roughness component 1250 can be on the top surface 106 of the transparent screen 104.

FIGS. 12-22 illustrate various embodiments of configurations that can be utilized to irradiate targeted items with electronic devices like in the example depicted in FIG. 9, as well as to disinfect the displays of the devices. It is understood that these configurations are not meant to be limited to use with mobile phone devices integrated with hand-held computer or personal digital assistant capabilities (e.g., a smartphone) as illustrated in the example of FIG. 9. Instead, the configurations and accompanying structures can be implemented with any electronic device that utilizes an ultraviolet transparent structure such as a screen, a display, or the like, that is subject to contamination through user contact and/or exposure from an ambient environment. For example, the configurations and accompanying structures described with respect to FIGS. 12-22 can also be implemented with a tablet computer, a laptop computer, a portable personal computer, a hand-held computerized device, a touchscreen monitor, a smart home appliance, an e-book, and/or the like.

FIG. 12 shows a schematic of an ultraviolet transparent structure 1300 having an ultraviolet diffusive layer 1302 configured for irradiation by a set of ultraviolet radiation sources 108 according to an embodiment. The ultraviolet transparent structure 1300 and the ultraviolet diffusive layer 1302 facilitate the transmission of ultraviolet radiation 1304 generated from the ultraviolet radiation sources 108. The ultraviolet radiation 1304 can undergo TIR and pass through an internal surface 1306 of the ultraviolet transparent structure 1300 and out of an external surface 1308 into an ambient environment 1310. In this manner, the ultraviolet radiation 1304 generated from the ultraviolet radiation sources 108 can be used to disinfect the external surface 1308 of the ultraviolet transparent structure 1300, an item or object that is placed on the external surface or that is situated a predetermined distance away from the external surface.

In one embodiment, the ultraviolet transparent structure 1300, like the aforementioned ultraviolet transparent screen 104 can include an ultraviolet transparent polymer. Examples of an ultraviolet transparent polymer, include but are not limited to, fluorinated ethylene propylene (FEP), fluorinated ethylene propylene co-polymer (EFEP), polyactic acid (PLA), low-density polyethylene (LDPE), and/or the like. The ultraviolet transparent structure 1300 can further include other materials such as for example, sapphire, crystal AlN, silicon carbide, fused silica, etc.

As used herein, an ultraviolet diffusive layer 1302 means a layer, a film or a coating that is transparent to ultraviolet light and that spreads or scatters the ultraviolet light in multiple different directions. The ultraviolet diffusive layer 1302 can include, but is not limited to, Gore® ePTFE, a fluoropolymer such as for example, FEP, EFEP, PLA, LDPE, etc., $SiO_2$, $Al_2O_3$, $CaF_2$, $MgF_2$, and/or the like. In one embodiment, the ultraviolet diffusive layer 1302 can be formed on another transparent layer of the ultraviolet transparent structure 1300 and act as the external surface 1308 of the structure that is exposed to the ambient environment 1310, which may have the need for a disinfection treatment or used to facilitate a treatment of an item placed on the surface or away from it.

The ultraviolet diffusive layer 1302 can have an index of refraction that is greater than the index of refraction of the ultraviolet transparent structure 1300. For example, in one embodiment the ultraviolet diffusive layer 1302 can have a minimum index of refraction of 1.5, while the ultraviolet transparent structure 1300 can have an index of refraction that ranges from approximately 1.0 to 1.47. Having the ultraviolet diffusive layer 1302 with an index of refraction that is greater than the index of refraction of the ultraviolet transparent structure is advantageous in minimizing Fresnel losses due to reflection on the border.

In one embodiment, the set of ultraviolet radiation sources 108 can include a first set of ultraviolet radiation sources configured to generate a scattered type of radiation that uniformly disinfects the external surface 1308 of the ultraviolet transparent structure 1302, and a second set of ultraviolet radiation sources configured to generate a focused type of radiation that disinfects at least one portion of the targeted item that can be positioned on or away from the external surface. For example, the set of ultraviolet radiation sources that generate the scattered radiation can be used to uniformly disinfect the external surface 1308 of the ultraviolet transparent structure 1300, while the other set of ultraviolet radiation sources that generate the focused radiation can be used to irradiate a specific surface of a portion of the item. The ultraviolet radiation sources of the various sets can operate with a multiple of wavelengths. For example, the ultraviolet radiation sources of a first set can operate with at least one wavelength in the UV-A range (e.g., 360 nm to 420 nm) and the ultraviolet radiation sources of a second set can operate with at least one wavelength in the UV-C range (e.g., 260 nm to 290 nm). In one embodiment, the ultraviolet radiation sources of a subset of the first or second set of ultraviolet radiation sources can operate in the UV-B range. It is understood that the set of ultraviolet radiation sources 108 can include more than two sets of ultraviolet radiation sources, or only one set with the set divided up into multiple sub-sets of sources.

The control system 15 described with respect to FIG. 2 can be configured to manage the ultraviolet radiation 1304 generated from the set of ultraviolet radiation sources 108. For example, the control system 15 can direct a first set of ultraviolet radiation sources 108 to generate the scattered type of radiation towards the external surface 1308 of the ultraviolet transparent structure 1300 and direct the second set of ultraviolet radiation sources to generate the focused type of radiation at the targeted item. In one embodiment, the control system 15 can direct the first set of ultraviolet radiation sources to generate the scattered type of radiation in response to ascertaining that a first set of attributes relating to the external surface of the ultraviolet transparent structure are indicative of a need for a disinfection operation (e.g., the surface is contaminated) or in response to a user selection expressing a desire to perform a disinfection operation of the external surface. This set of attributes can include any of the aforementioned parameters (e.g., frequency of usage, disinfection schedule history, presence of biological activity (e.g., measured bacteria), growth rate of organisms, etc.), however it is understood that these parameters are only illustrative and not meant to limit the various embodiments. In addition, the control system 15 can direct the second set of ultraviolet radiation sources to generate the focused type of radiation at the targeted item in response to a user selection expressing a desire to disinfect the targeted item and/or in response to determining that the targeted item is located on the external surface.

The control system 15 can be further configured to monitor the first set of attributes while the first set of ultraviolet radiation sources performs a disinfection operation on the external surface 1308 of the ultraviolet transparent structure 1300, and monitor a second set of attributes relating to a surface of the targeted item while the second set of ultraviolet radiation sources performs a disinfection operation on the item. The second set of attributes can include, but are not limited to, any of the aforementioned parameters (associated with the item that is to be irradiated). To this extent, the control system 15 can adjust the radiation generated from the first set of ultraviolet radiation sources as a function of the monitored first set of attributes, and adjust the radiation generated from the second set of ultraviolet radiation sources as a function of the monitored second set of attributes. In this manner, the sets of ultraviolet radiation sources can be used to disinfect the external surface 1308 and/or the targeted item. It is understood that the control system 15 can direct the various sets of ultraviolet radiation sources to operate simultaneously such that both of the external surface 1308 and the item undergo a disinfection operation.

FIG. 13 shows a schematic of the ultraviolet transparent structure 1300 having an ultraviolet diffusive layer 1312 with a plurality of ultraviolet diffusive protrusions 1314 configured for irradiation by the set of ultraviolet radiation sources 108 according to an embodiment. The plurality of ultraviolet diffusive protrusions 1314 can be designed to extract the ultraviolet radiation generated from the set of ultraviolet radiation sources 108 from within the ultraviolet transparent structure 1300. In one embodiment, each of the ultraviolet diffusive protrusions 1314 can be separated from an adjacent diffusive protrusion by a predetermined spacing

1316. Each ultraviolet diffusive protrusion 1314 can form a light emitting protrusion region. In this manner, each ultraviolet diffusive protrusion 1314 can be configured to extract ultraviolet radiation from the set of ultraviolet radiation sources 108 to the external surface 1308 of the ultraviolet diffusive layer 1312 and/or to the targeted item.

It is understood that the ultraviolet diffusive layer 1312 depicted in FIG. 13 can be configured according to other structures, and thus is not meant to be limiting. For example, the ultraviolet diffusive layer 1312 can be configured to have roughness elements that facilitate light diffusion from the ultraviolet transparent structure 1300. In one embodiment, the roughness elements can be formed with one or more of the ultraviolet diffusive protrusions 1314 or apart from the protrusions, e.g., formed near a top surface 1308 of the ultraviolet diffusive layer 1312.

In an alternative to the embodiments depicted in FIGS. 12 and 13, the ultraviolet diffusive layer can include a discontinuous layer with discontinuous regions of ultraviolet diffusive material. The discontinuous regions of ultraviolet diffusive material, which can include any of the aforementioned materials, can extend laterally over the ultraviolet transparent structure 1300. In addition, each discontinuous region can be configured to extract light with a predetermined target property that can include, but is not limited to a predetermined light angle distribution width, predetermined light direction, etc. For example, a microlens-shaped surface can cause the extracted light to have a narrow angular diameter. As another example, a light diffusive surface with micro-roughness can cause the extracted light to have a wide angular diameter. In one embodiment, the discontinuous regions of ultraviolet diffusive material can be placed non-uniformly over the external surface of the ultraviolet transparent structure 1300. It is understood that the discontinuous regions of ultraviolet diffusive material can also be placed uniformly over the external surface of the ultraviolet transparent structure 1300. In one embodiment, the discontinuous layer with discontinuous regions of ultraviolet diffusive material can be formed as part of the external surface 1308 of the ultraviolet transparent structure 1300.

FIG. 14 shows a schematic of the ultraviolet transparent structure 1300 and the ultraviolet diffusive layer 1302 in a configuration similar to the one depicted in FIG. 12, except that in this embodiment at least one of the ultraviolet radiation sources 108 is optically coupled to the structure with an optical element 1318 according to an embodiment. In this manner, the optical element 1318 can focus and direct the ultraviolet radiation generated from the ultraviolet radiation sources 108 to the internal surface 1306 of the ultraviolet transparent structure 1300. The optical element 1318 can include, but is not limited to, optical fibers, a lens, optical fibers with optical lenses, waveguiding UV-encapsulating material, etc. As shown in FIG. 14, the optical element 1318 can be applied directly to a bottom surface at one side, while applied directly to the emitting face of a respective ultraviolet radiation source 108.

In one embodiment, the optical element 1318 can include a waveguiding optical element (e.g., optical fiber or custom shaped encapsulating material) with surfaces 1320 that control and diffuse the light from a respective ultraviolet radiation source 108 throughout the ultraviolet transparent structure 1300. The optical element 1318 can be bonded to the bottom surface of the ultraviolet transparent structure 1300 and an emitting face of an ultraviolet radiation source via bonding domains 1322A and 1322B, respectively. Examples of material that are suitable for use as the bonding domains 1322A and 1322B can include, but are not limited to, UV silicones, as for example, CYTOP® amorphous fluoropolymer, GORE® ePTFE, a fluoropolymer (e.g., FEP, EFEP, PLA, LDPE, etc.), $SiO_2$, $Al_2O_3$, $CaF_2$, $MgF_2$, and/or the like.

The indexes of refraction for the optical element 1318 and the bonding domains 1322A and 1322B can be configured to create a desired reflection effect within the ultraviolet transparent structure 1300 by choosing a difference between the indexes of refraction the optical element 1318 and the bonding domains 1322A and 1322B. In one embodiment, the optical element 1318 can have an index of refraction that is higher than the ambient environment 1310 which can be air, while an interface 1324 between the optical element and the ambient acts as a partially reflective surface due to the total internal reflection occurring for some of the incoming irradiation. In this manner, the reflected rays enter the ultraviolet transparent structure 1300 due to index matched bonding of the optical element 1318 and the structure. This index matched bonding assumes that the bonding material of the bonding domains 1322A and 1322B has a refractive index that is in vicinity of the refractive indices of the material of the ultraviolet transparent structure 1300 and the material of the optical element 1318. In an embodiment, the refractive index of the bonding material for the bonding domains 1322A and 1322B can comprise an index of about 1.3 and the refractive index of the ultraviolet transparent structure 1300 can comprise about 1.8. Thus, in this embodiment the difference between the refractive indices of the bonding material for the bonding domains 1322A and 1322B and the material for the ultraviolet transparent structure 1300 can be as much as 40% to 50%.

FIG. 15 shows a schematic of an ultraviolet transparent structure 1326 having a prismatic shape with non-parallel surfaces 1328 (1328A, 1328B, 1328C, 1328D, 1328E), a partially reflective and partially transmissive layer 1330 and a cover 112 placed over one of the non-parallel surfaces of the structure according to an embodiment. In one embodiment as shown in FIG. 15, the set of ultraviolet radiation sources 108 can be coupled to the surface 1328B, however, it is understood that other surfaces of the prismatic-shaped ultraviolet transparent structure 1326 can have one or more ultraviolet radiation sources coupled in addition to, or in place of the coupling at the surface 1328B. The partially reflective and partially transmissive layer 1330 can be formed adjacent to or over the external surface of the ultraviolet transparent structure 1326 which in FIG. 15 can include the surface 1328C. As used herein, a partially reflective and partially transmissive layer is a layer that includes regions, portions or domains that are partially reflective to ultraviolet light of a particular wavelength (e.g., has an ultraviolet reflection coefficient in a range 0.35-0.65), and regions, portions or domains that are transparent to ultraviolet light of a particular wavelength such that at least ten percent of the ultraviolet radiation can pass there through at a normal.

In one embodiment, the partially reflective and transparent layer 1330 can include a first portion 1332 that is configured to reflect light generated from the set of ultraviolet radiation sources 108 back to the internal surface 1328A of the ultraviolet transparent structure 1326 for facilitating waveguiding of the light within the ultraviolet transparent structure, and a second portion 1334 that is configured to transmit light generated from the set of ultraviolet radiation sources through the external surface 1328C of the ultraviolet transparent structure 1324 and/or through the external surface to a targeted item. The first portion 1332 and the second portion 1334 can take the form of separate layers, coatings or films that are distinct from the ultraviolet transparent structure 1326, or formed as the top external surface of the structure. It is understood that the first portion 1332 and the second portion 1334 can be configured according to other arrangements. Thus, the implementation depicted in FIG. 15 is not meant to be limiting.

Like some of the other embodiments described herein, the cover 112 in FIG. 15 can be configured to cover at least the external surface 1328C of the ultraviolet transparent structure 1326. For example, the cover 112 can include a first surface 1336 having a reflective layer facing the external surface 1328C of the ultraviolet transparent structure 1326 in a closed position. In this manner, the first surface 1336 of the top cover 112 ensures that the ultraviolet radiation does not exit the ultraviolet transparent structure 1326 from either the first portion 1332 or the second portion 1334 of the partially reflective and transparent layer 1330. The cover 112 also includes a second surface 1338 opposing the first surface 1336 with exposure to the ambient environment 1310 in both an open position and a closed position.

As noted above, the cover 112 can be implemented with the aforementioned fins 218. For example, the fins 218 can extend from the cover 112 into the first portion 1332 and the second portion 1334 of the partially reflective and transparent layer 1330 in the closed position. To this extent, the fins 218 can provide a boundary between the cover 112 and the partially reflective and transparent layer 1330 including the surface 1328C of the ultraviolet transparent structure 1326. In particular, each of the fins contacts a separate portion of the partially reflective and transparent layer 1330 and/or the surface 1328C of the ultraviolet transparent structure 1326 in the closed position, such that a layer of air is located between the cover 112 and these elements in each spacing formed between adjacent fins.

In addition to treating the external surface of the ultraviolet transparent structure, the various embodiments can be used to disinfect items placed on the structure or items that are within an irradiation coverage range of the ultraviolet radiation generated from the ultraviolet radiation sources. FIG. 16 shows a schematic of items 1340 placed on the ultraviolet transparent structure 1300 depicted in FIG. 12 with the set of ultraviolet radiation sources 108 used to disinfect the items according to an embodiment. In the example depicted in FIG. 16, the items 1340 are apples, however, it is understood that this type of object is only one example of possible items that can be disinfected with the embodiments described herein. In general, the type of items or objects that are suitable for on-board ultraviolet transparent structure disinfection will depend on the size of the items and the electronic device that incorporates the ultraviolet transparent structure and accompanying components that facilitate the irradiation.

The on-board ultraviolet disinfection of item(s) placed on the external surface of the structure including any of the additional layers used with the external surface (e.g., an ultraviolet diffusive layer, a partially reflective and partially transmissive layer) can be performed according to one of a number of different approaches. For example, in one embodiment, a user 12 (FIG. 2) can interact with the control system 15 to manually activate the set of ultraviolet radiation sources 108 to perform a disinfection operation of the items 1340. As noted above, the control system 15 can direct the ultraviolet radiation sources 108 to irradiate the items 1340 in one of a number of approaches. For example, the control system 15 can direct the ultraviolet radiation sources 108 to irradiate the items 1340 with varying types of ultraviolet radiation (e.g., UV-A, UV-B and UV-C), at different wavelengths, intensities, patterns, and duration. In one embodiment, the ultraviolet radiation sources 108 can operate for a predetermined time that is known to be sufficient to disinfect the type of object or at a time that is known to eradicate a wide variety of micro-organisms, bacteria, viruses, and the like. The user 12 can also terminate the disinfection operation by manually instructing the control system 15 to turn off the ultraviolet radiation sources 108.

In another approach, the control system 15 can use one or more sensing devices 38 to facilitate an on-board ultraviolet disinfection operation of the items. The sensing devices 38 can include one or more of any of the aforementioned sensing devices used singly or in combination. In one embodiment, one or more sensing devices can include mechanisms capable of detecting the presence of an item or object on the external surface of the ultraviolet transparent structure. These item sensing devices can take the form of a number sensors that include, but are not limited to, proximity sensors (e.g., capacitance, optical, magnet, mechanical contact proximity sensors), pressure sensors, and the like. For example, a pressure sensor can measure the pressure experienced by the external surface of the ultraviolet transparent structure, while a proximity sensor can determine the proximity of an item to the external surface of the ultraviolet transparent structure. In either case, the sensing devices 38 can generate signals representative of the conditions that each is configured to detect and send those signals to the control system which uses this information to determine the presence of the item, the type of item (e.g., a food item, a person's finger) touching the structure, properties associated with the touch (e.g., weight). The control system 15 can then initiate a disinfection operation depending on its assessment of the data from the sensing devices 38 by activating the set of ultraviolet radiation sources 108.

FIG. 17 shows a schematic illustrating the ultraviolet transparent structure 1300 operating in conjunction with at least one item sensing device 38 and the control system 15 to irradiate items according to an embodiment. In the example depicted in FIG. 17, the items that can be detected by the item sensing device 38 include a piece of fruit 1342 (e.g., a strawberry) and a person's finger 1344. However, it is understood that the sensing device 38 in conjunction with the control system 15 can detect information associated with other types of objects and effectuate a disinfection operation of these objects and any other bodies capable of contaminating the external surface 1308 of the ultraviolet transparent structure 1300. In this embodiment, the item sensing devices 38 can detect the presence of the strawberry 1342 and/or the touch of the person's finger 1344, and send the information about the touch and the location of the touch of the items to the control logic of the control system 15 designed to control the ultraviolet radiation sources 108. In an embodiment, the item sensing device 38 can detect the presence and location of the strawberry 1342 and/or the person's finger 1344 with respect to a predetermined proximity distance from the external surface 1308 of the ultraviolet transparent structure 1300.

It is understood that other sensing devices 38 can be used in addition to the aforementioned item sensing devices, or in embodiments that do not utilize such devices. For example, at least one sensor operating in conjunction with the set of ultraviolet radiation sources 108 and the control system 15 can be used to obtain conditional data associated with the external surface 1308 of the ultraviolet transparent structure 1300 and any targeted item. As used herein conditional data means the contamination conditions associated with the external surface 1308 of the ultraviolet transparent structure 1300 and the targeted item. The contamination conditions can include, but are not limited to, the presence, the location, the type and the degree of contamination on the external surface 1308 of the ultraviolet transparent structure 1300 and the targeted item, and the duration that the contamination has resided on the structure.

Any of the aforementioned sensing devices including, but not limited to, a bacterial fluorescence sensor, a temperature sensor, a chemical sensor, a humidity sensor, a visual camera, and the like, can be used to sense conditional data. Each of these sensors can detect the level or amount of a particular parameter that each is intended to measure and send signals thereof to the control system 15 which can use the information to initiate a disinfection operation with the ultraviolet radiation sources 108. The control system 15 can also monitor the disinfection operation, and adjust any parameters of the sources depending on the results of the monitored conditions. In one embodiment, the control system 15 can use the information to determine the last time that the item underwent a disinfection process, and select an optimal power setting to be supplied to the ultraviolet radiation sources 108 to effectuate the disinfection process. The control system 15 can select a power setting based on the proximity of a particular ultraviolet radiation source to a site on the external surface 1308 of the ultraviolet transparent structure 1300 and/or the surface of the item that has contamination.

In addition to sensing conditional data, one or more sensing devices can be used to detect irradiation data associated with the radiation generated from the ultraviolet radiation sources 108. As used herein, irradiation data includes information relating to the wavelength, the intensity, the duration, the frequency, and the pattern of the radiation generated from the sources. Spectrophotometers and radiation sensors are only a couple of examples of sensors that can be used obtain irradiation data during a disinfection operation. Other sensors include, but are not limited to, broadband and band-pass photodetectors, optical dosage sensors (e.g., paper-strip-based), etc. The control system 15 can use the irradiation data to monitor the disinfection operation of the item, and adjust any parameters of the sources depending on the results of the monitored conditions.

Figure 18:
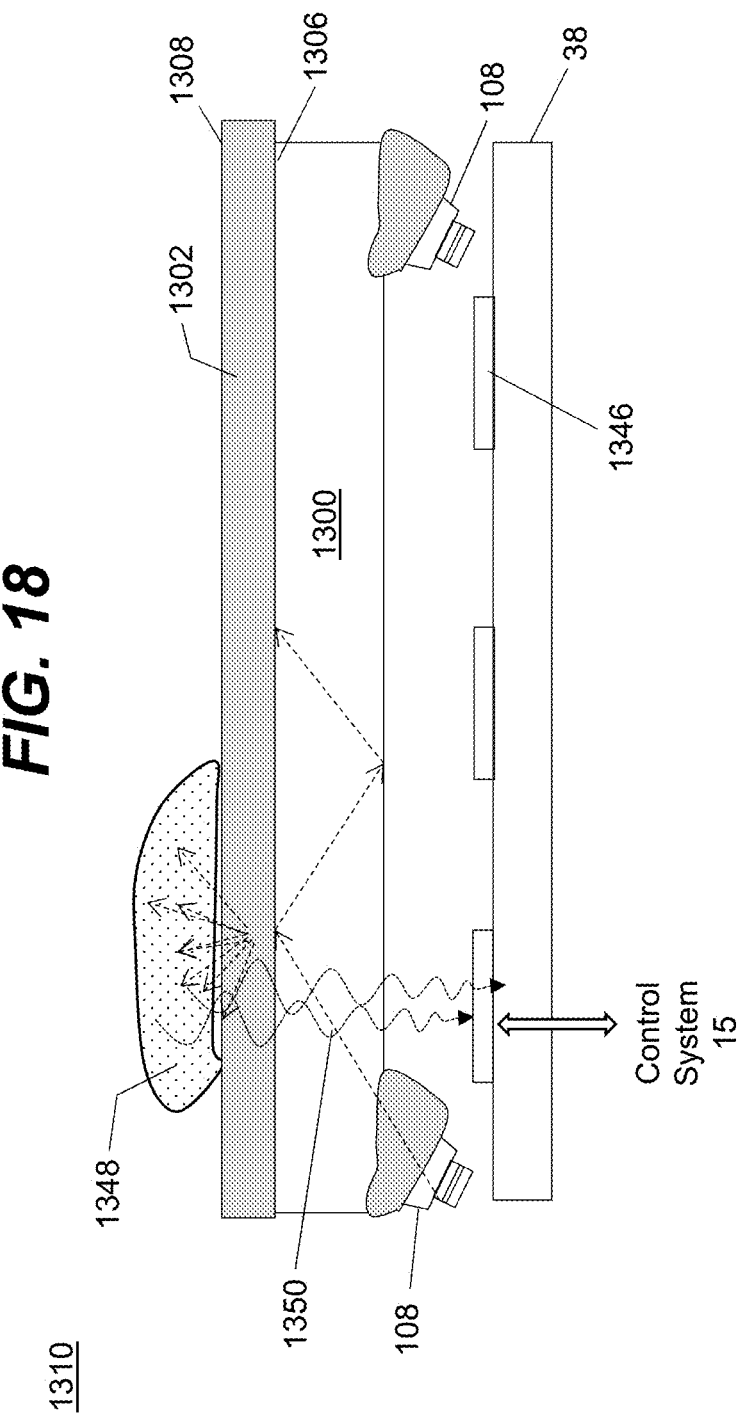
FIG. 18 shows a schematic illustrating an ultraviolet transparent structure operating in conjunction with at least one sensing device and a control system to irradiate an item as a function of fluorescence measurements according to an embodiment.

FIG. 18 shows a schematic illustrating the ultraviolet transparent structure 1300 operating in conjunction with a sensing device 38 that includes one or more bacterial fluorescent sensors 1346 and the control system 15 to irradiate an item 1348 on the external surface 1308 of the structure as a function of fluorescence measurements according to an embodiment. In this embodiment, each bacterial fluorescent sensor 1346 can detect fluorescence radiation 1350 generated from the external surface 1308 of the ultraviolet transparent structure 1300 and/or the targeted item 1348 after irradiation by the set of ultraviolet radiation sources 108. The reflected/emitted fluorescence radiation 1350 from the item 1348 can be detected by the fluorescent sensors 1346 and the fluorescence data can be passed onto the control system 15 to assess the contamination conditions. The control logic of the control system 15 will adjust irradiation parameters if necessary and continue monitoring the disinfection process until a surface of the item 1348 has been sufficiently disinfected based on a continued assessment of the fluorescence data.

It is understood that there are a wide number of configurations that can be implemented with the aforementioned sensing devices and that the various embodiments of the present invention are not meant to be limited to any one in particular. For example, the embodiment depicted in FIG. 18 can be implemented with any of the aforementioned item sensing devices and used along with the fluorescent sensors 1346 to manage the disinfection operation of the external surface 1308 of the ultraviolet transparent structure 1300 and/or the item 1348.

The ultraviolet transparent structure of the various embodiments described herein can be configured with a waveguiding component to further facilitate use of the ultraviolet radiation generated from the set of ultraviolet radiation sources 108 in the disinfection of the external surface of the structure and/or any items placed thereon or that are within the irradiation coverage of the sources. In general, the waveguiding component can be positioned between the external surface and the internal surface of the ultraviolet transparent structure for waveguiding the ultraviolet radiation generated from the set of ultraviolet radiation sources.

FIGS. 19A-19C show schematic views of an ultraviolet transparent structure 1352 having an waveguiding component 1354 with a set of individual waveguiding components 1356 each configured to waveguide segments of the ultraviolet radiation according to an embodiment. As shown in FIG. 19A, the ultraviolet transparent structure 1352 can include an attachment domain 1358 coupled to the waveguiding component 1354 and the set of ultraviolet radiation sources 108. The attachment domain 1358 can extend vertically from an external surface 1360 of the ultraviolet transparent structure 1352 to an internal surface 1362. In one embodiment, the set of ultraviolet radiation sources 108 can be bonded to the attachment domain 1358 by a bonding domain 1322 that can include any of the above-mentioned ultraviolet transparent bonding materials, while the set of individual waveguiding components 1356 can be bonded to the attachment domain 1358 by similar materials. With this configuration, the set of individual waveguiding components 1356 can distribute the ultraviolet radiation generated from the ultraviolet radiation sources throughout the ultraviolet transparent structure 1352 so that the radiation can travel towards the external surface 1360 for disinfection of the surface and/or any item placed thereon or within its proximity.

FIG. 19B shows a more detailed view of a portion of one of the individual waveguiding components 1356 depicted in FIG. 19A. As shown in FIG. 19B, each individual waveguiding component 1356 can include a first reflective layer 1364, a second reflective layer 1366, a transparent core 1368 positioned between the first reflective layer and the second reflective layer, and a plurality of supporting elements 1370 supporting the transparent core in a predetermined position with respect to the first reflective layer and the second reflective layer. To this extent, the transparent core 1368 can maintain separation from both the first reflective layer 1364 and the second reflective layer 1366, ensuring that each element is able to perform its intended functions (i.e., reflection and transmission of light) without interference from one another. It is understood that this structure of the of individual waveguiding components 1356 represents one possible construction and is not meant to be limiting.

FIG. 19C shows that the individual waveguiding components 1356 of the waveguiding component 1354 can have bending flexibility. This configuration is beneficial in that the waveguiding component 1354 can have an ability to form and/or to direct radiation to complex-shaped external surfaces and/or object for UV-disinfection purposes. Such a configuration may be particularly useful in applications that entail cleaning tools, like brushes, e.g., tooth brushes. With UV-transparent fibers forming the working brush element and illuminated from an internal UV light source, the effectiveness of UV-disinfection of each fiber of the brush can be as high as 100%, which can be significantly better as compared with external source UV disinfection, where shading can limit the effectiveness of the UV disinfection.

FIGS. 20-22 show additional embodiments of waveguiding components that can be utilized with the various ultraviolet transparent structures described herein in order to efficiently waveguide light generated from the ultraviolet radiation sources for purposes of facilitating a disinfection operation. FIG. 20 shows a schematic of a waveguiding component 1372 having an elongated body 1374 that can be utilized with an ultraviolet transparent structure according to an embodiment. In this embodiment, the ultraviolet radiation generated from the ultraviolet radiation source 108 that is coupled to the waveguiding component 1372 via the attachment domain 1358 can undergo TIR which is useful in instances where the waveguiding component is used to uniformly disinfect an external surface of an ultraviolet transparent structure. FIG. 21 shows a schematic of a waveguiding component 1376 having an elongated body 1378 with roughness elements 1380 located at multiple locations including opposing exterior surfaces of the elongated body. The roughness elements 1380 can facilitate the diffusion (i.e., extraction and emission) of the light from the ultraviolet radiation sources which is useful for disinfection operations. FIG. 22 shows a schematic of a waveguiding component 1382 having a main waveguiding body 1384 and at least two waveguiding branching members 1386, 1388 each emanating from the main waveguiding body that can be utilized with an ultraviolet transparent structure. This configuration can be advantageous for the UV disinfection of cleaning tools, e.g., brushes, for fine and hardly reachable objects, especially with sub-millimeter dimensions. It is understood that the waveguiding components depicted in FIGS. 20-22 are illustrative of only a few examples of possible arrangements and shapes that can be used with ultraviolet transparent structures described herein to facilitate disinfection operations and are not meant to be limiting.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An apparatus, comprising:
an ultraviolet transparent structure having an external surface with exposure to an ambient environment and an internal surface separated from the ambient environment by the external surface;
a set of ultraviolet radiation sources configured to generate ultraviolet radiation through the internal surface of the ultraviolet transparent structure towards the external surface and out to the ambient environment for disinfection of the external surface and/or a targeted item located off of the ultraviolet transparent structure, wherein the set of ultraviolet radiation sources includes a first set of ultraviolet radiation sources configured to generate a scattered type of radiation that uniformly disinfects the external surface of the ultraviolet transparent structure and a second set of ultraviolet radiation sources configured to generate a focused type of radiation that disinfects at least one portion of the targeted item; and
a control system configured to manage the ultraviolet radiation generated from the set of ultraviolet radiation sources, the control system directing the first set of ultraviolet radiation sources to generate the scattered type of radiation towards the external surface of the ultraviolet transparent structure and the second set of ultraviolet radiation sources to generate the focused type of radiation at the targeted item.

2. The apparatus of claim 1, wherein the control system directs the first set of ultraviolet radiation sources to generate the scattered type of radiation in response to ascertaining that a first set of attributes relating to the external surface of the ultraviolet transparent structure indicate a need for a disinfection operation or in response to a user selection expressing a desire to perform a disinfection operation of the external surface.

3. The apparatus of claim 2, wherein the control system is configured to monitor the first set of attributes while the first set of ultraviolet radiation sources performs a disinfection operation of the external surface of the ultraviolet transparent structure, and wherein the control system is configured to monitor a second set of attributes relating to a surface of the targeted item while the second set of ultraviolet radiation sources performs a disinfection operation of the item.

4. The apparatus of claim 3, wherein the control system is configured to adjust the radiation generated from the first set of ultraviolet radiation sources as a function of the monitored first set of attributes, and adjust the radiation generated from the second set of ultraviolet radiation sources as a function of the monitored second set of attributes.

5. The apparatus of claim 1, wherein the set of ultraviolet radiation sources is further configured to irradiate the targeted item in response to a placement of the item on the external surface of the ultraviolet transparent structure, wherein the control system directs the operation of the second set of ultraviolet radiation sources upon a determination that there is a placement of the targeted item on the external surface, the control system monitoring the second set of attributes of the targeted item while undergoing irradiation and adjusting operation of the second set of ultraviolet radiation sources as a function of the monitored second set of attributes.

6. The apparatus of claim 1, further comprising an ultraviolet diffusive layer formed adjacent to the external surface of the ultraviolet transparent structure, wherein the ultraviolet diffusive layer separates the external surface from the ambient environment.

7. The apparatus of claim 6, wherein the ultraviolet diffusive layer comprises a plurality of diffusive protrusions each separated from an adjacent diffusive protrusion by a predetermined spacing, each predetermined spacing between the diffusive protrusions forming light emitting protrusion regions, wherein the plurality of diffusive protrusions are configured to extract ultraviolet radiation from the set of ultraviolet radiation sources through at least one of the light emitting protrusion regions to the external surface of the ultraviolet transparent structure and/or to the target item.

8. The apparatus of claim 7, wherein at least one of the plurality of diffusive protrusions comprises roughness elements.

9. The apparatus of claim 6, wherein the ultraviolet diffusive layer comprises a plurality of discontinuous regions of ultraviolet diffusive material.

10. The apparatus of claim 9, wherein the plurality of discontinuous regions are non-uniformly placed over the external surface of the ultraviolet transparent structure, each discontinuous region configured to extract light with a predetermined target property.

11. The apparatus of claim 1, further comprising at least one optical element coupled to one of the ultraviolet radiation sources, wherein the at least one optical element couples the ultraviolet radiation source to the internal surface of the ultraviolet transparent structure.

12. The apparatus of claim 1, wherein the ultraviolet transparent structure comprises a prismatic shape having non-parallel surfaces.

13. The apparatus of claim 1, further comprising a partially reflective and partially transmissive layer formed adjacent to the external surface of the ultraviolet transparent structure, wherein the partially reflective and partially transmissive layer comprises a first portion that is configured to reflect light generated from the set of ultraviolet radiation sources back to the internal surface of the ultraviolet transparent structure for facilitating waveguiding of the light within the ultraviolet transparent structure, and a second portion that is configured to transmit light generated from the set of ultraviolet radiation sources to the external surface of the ultraviolet transparent structure and/or through the external surface to the targeted item.

14. The apparatus of claim 1, wherein at least a portion of the external surface of the ultraviolet transparent structure comprises a roughness element configured to scatter light generated from the set of ultraviolet radiation sources.

15. The apparatus of claim 1, further comprising at least one sensor operating in conjunction with the set of ultraviolet radiation sources and the control system to obtain conditional data associated with the external surface of the ultraviolet transparent structure and the targeted item, and irradiation data associated with the radiation generated from the set of ultraviolet radiation sources, wherein the control system is configured to control the irradiation of the external surface and the targeted item as a function of the conditional data and the irradiation data.

16. The apparatus of claim 15, wherein the at least one sensor includes a set of fluorescent sensors each configured to detect fluorescence radiation generated from the external surface of the ultraviolet transparent structure and/or the targeted item after irradiation by the set of ultraviolet radiation sources, wherein the control system is configured to control the irradiation of the external surface and the targeted item as a function of the detected fluorescence radiation.

17. The apparatus of claim 1, wherein the ultraviolet transparent structure further comprises a waveguiding component positioned between the external surface and the internal surface for waveguiding the ultraviolet radiation generated from the set of ultraviolet radiation sources.

18. The apparatus of claim 17, wherein the waveguiding component includes one of a set of individual waveguiding components each configured to waveguide segments of the ultraviolet radiation, a waveguiding elongated body with a set of roughness elements formed on an exterior surface of the elongated body, and a main waveguiding body with at least two waveguiding branching members each emanating from the main waveguiding body.

19. An apparatus, comprising:
an ultraviolet transparent structure having an external surface with exposure to an ambient environment, and an internal surface separated from the ambient environment by the external surface;
a set of ultraviolet radiation sources configured to generate ultraviolet radiation through the internal surface of the ultraviolet transparent structure towards the external surface and out to the ambient environment for disinfection of the external surface and/or a targeted item located off of the ultraviolet transparent structure, wherein the set of ultraviolet radiation sources includes a first set of ultraviolet radiation sources configured to generate a scattered type of radiation that uniformly disinfects the external surface of the ultraviolet transparent structure and a second set of ultraviolet radiation sources configured to generate a focused type of radiation that disinfects at least one portion of the targeted item;
at least one sensor configured to obtain conditional data associated with the external surface of the ultraviolet transparent structure and the targeted item, and irradiation data associated with the radiation generated from the set of ultraviolet radiation sources, and
a control system configured to operate in conjunction with the set of ultraviolet radiation sources and the at least one sensor, the control system directing the first set of ultraviolet radiation sources to generate the scattered type of radiation towards the external surface of the ultraviolet transparent structure and directing the second set of ultraviolet radiation sources to generate the focused type of radiation at the targeted item, wherein the control system directs operation of the first and the second set of ultraviolet radiation sources as a function of the conditional data and irradiation data obtained from the at least one sensor.

20. An apparatus, comprising:
an ultraviolet transparent structure having an external surface with exposure to an ambient environment, and an internal surface separated from the ambient environment by the external surface;
a set of ultraviolet radiation sources configured to generate ultraviolet radiation through the internal surface of the ultraviolet transparent structure towards the external surface and out to the ambient environment for disinfection of the external surface and/or a targeted item located off of the ultraviolet transparent structure, wherein the set of ultraviolet radiation sources includes a first set of ultraviolet radiation sources configured to generate a scattered type of radiation that uniformly disinfects the external surface of the ultraviolet transparent structure and a second set of ultraviolet radiation sources configured to generate a focused type of radiation that disinfects at least one portion of the targeted item;
a cover configured to cover the ultraviolet transparent structure to prevent transmission of ultraviolet radiation to the ambient environment in a closed position, wherein the cover includes a first surface having a reflective layer facing the external surface of the ultraviolet transparent structure in the closed position and a second surface opposing the first surface with exposure to the ambient environment in both an open position and a closed surface; and
a control system configured to manage the ultraviolet radiation generated from the set of ultraviolet radiation sources, the control system directing the first set of ultraviolet radiation sources to generate the scattered type of radiation towards the external surface of the ultraviolet transparent structure and directing the second set of ultraviolet radiation sources to generate the focused type of radiation at the targeted item.

\* \* \* \* \*